United States Patent
Ikeda et al.

(10) Patent No.: US 7,282,575 B2
(45) Date of Patent: Oct. 16, 2007

(54) FUNCTIONAL PEPTIDE NUCLEIC ACID MONOMER AND PROCESS FOR PRODUCING THE SAME

(75) Inventors: Hisafumi Ikeda, Chiba (JP); Isao Saito, Kyoto (JP); Fumihiko Kitagawa, Aichi (JP)

(73) Assignee: Credia Japan Co., Ltd., Kyoto (JP)

( * ) Notice: Subject to any disclaimer, the term of this patent is extended or adjusted under 35 U.S.C. 154(b) by 362 days.

(21) Appl. No.: 10/250,592

(22) PCT Filed: Sep. 19, 2001

(86) PCT No.: PCT/JP01/08120

§ 371 (c)(1),
(2), (4) Date: Dec. 24, 2003

(87) PCT Pub. No.: WO02/051797

PCT Pub. Date: Jul. 4, 2002

(65) Prior Publication Data

US 2004/0101839 A1    May 27, 2004

(30) Foreign Application Priority Data

Dec. 26, 2000   (JP)   ............... 2000-394669

(51) Int. Cl.
| C07C 245/08 | (2006.01) |
| C07C 271/20 | (2006.01) |
| C07D 221/04 | (2006.01) |
| C07D 311/12 | (2006.01) |
| C07D 311/16 | (2006.01) |
| C07D 311/80 | (2006.01) |
| C07D 475/14 | (2006.01) |
| C07D 491/22 | (2006.01) |
| C07D 495/04 | (2006.01) |

(52) U.S. Cl. ............ 534/732; 534/798; 544/251; 546/37; 546/98; 546/99; 546/157; 548/303.7; 549/227; 549/287; 549/288; 549/289; 549/388; 549/394; 560/27; 560/28

(58) Field of Classification Search ............... 534/798, 534/847, 851, 732; 544/251; 546/37, 98, 546/99, 157; 548/303.7; 549/227, 287, 549/288, 289, 388, 394; 560/27, 28

See application file for complete search history.

(56) References Cited

U.S. PATENT DOCUMENTS

| 5,714,331 | A  | 2/1998  | Buchardt et al. |
| 5,736,336 | A  | 4/1998  | Buchardt et al. |
| 5,766,855 | A  | 6/1998  | Buchardt et al. |
| 5,786,461 | A  | 7/1998  | Buchardt et al. |
| 5,977,296 | A  | 11/1999 | Nielsen et al. |
| 6,117,973 | A  | 9/2000  | Batz et al. |
| 6,201,103 | B1 | 3/2001  | Nielsen et al. |
| 6,225,052 | B1 | 5/2001  | Batz et al. |
| 6,617,422 | B1* | 9/2003 | Nielsen et al. ............ 530/300 |
| 6,809,190 | B2* | 10/2004 | Ikeda et al. ............. 536/23.1 |
| 6,919,476 | B2* | 7/2005 | Ikeda et al. ............. 560/159 |

FOREIGN PATENT DOCUMENTS

| EP | 1074559 | 2/2001 |
| WO | WO92/20702 | 11/1992 |
| WO | WO98/37232 | 8/1998 |

* cited by examiner

Primary Examiner—Fiona T Powers
(74) Attorney, Agent, or Firm—Richard M. Goldberg

(57) ABSTRACT

A compound represented by the general formula (I) below:

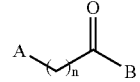

In the formula, A is as defined in the specification and B denotes

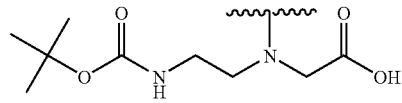

where n is an integer of 1 to 4, and a process for producing the above compound includes a reaction between an activated ester and a t-butoxycarbonylaminoethylamine or an ω-amino acid derivative.

1 Claim, 1 Drawing Sheet

Negatively charged

DNA

Peptide nucleic acid (PNA)

Charged neither positively nor negatively

Fmoc type PNA monomer unit

Boc type PNA monomer unit

FUNCTIONAL PEPTIDE NUCLEIC ACID MONOMER AND PROCESS FOR PRODUCING THE SAME

TECHNICAL FIELD

The present invention relates to a functional peptide nucleic acid monomer having a novel structure and a production process therefor.

BACKGROUND ART

Nucleic acids are the DNA and RNA that govern the genetic information of living creatures. On the other hand, a peptide nucleic acid (PNA) is a modified nucleic acid in which the sugar-phosphate skeleton of a nucleic acid has been converted into an N-(2-aminoethyl)glycine skeleton (FIG. 1). The sugar-phosphate skeletons of DNA/RNA are negatively charged under neutral conditions and exhibit electrostatic repulsion between the complementary strands, but since the backbone structure of PNA itself has no charge, there is no electrostatic repulsion. PNA therefore has a high duplex-forming ability and a high base sequence recognition ability in comparison with conventional nucleic acids. Furthermore, since PNA is very stable against in vivo nuclease/protease and is not decomposed thereby, its application in gene therapy as an antisense molecule has been investigated.

Modifying conventional techniques that employ DNA as a medium so that they can be used with PNA can compensate for the defects of DNA that could not be overcome previously. For example, it is possible to apply PNA to the "DNA microarray technology" that carries out a systematic analysis of a large amount of genetic information at high speed, and to the "molecular beacon" that has been developed recently as a probe that can detect by fluorescence a specifically recognised base sequence. Since these techniques use DNA as a medium, which has poor enzyme resistance, when employing these techniques it is necessary to carry out precise sampling. Satisfying this requirement is the key to enhancing the above-mentioned techniques.

On the other hand, since PNA is completely resistant to enzymes, the use of PNA as a replacement for DNA in the DNA microarray technology and the molecular beacon is anticipated to eliminate the defects of the above-mentioned techniques and to derive further advantages.

There are a large number of fields, in addition to the DNA microarray technology and the molecular beacon, that are anticipated to advance as a result of the use of PNA, and in these fields it is necessary to efficiently functionalise PNA, that is to say, to design a novel PNA monomer by the efficient introduction of a functional molecule to a PNA monomer.

Since methods for synthesising a PNA oligomer employ the commonly used solid phase peptide synthesis, PNA monomer units can be classified into two types in terms of the PNA backbone structure, that is to say, the Fmoc type PNA monomer unit and the tBoc type PNA monomer unit (FIG. 2).

A method for synthesising the Fmoc type PNA monomer unit has already been established, its oligomers can be synthesised by means of a standard automatic DNA synthesiser, and it can be synthesised on a small scale by the route below:

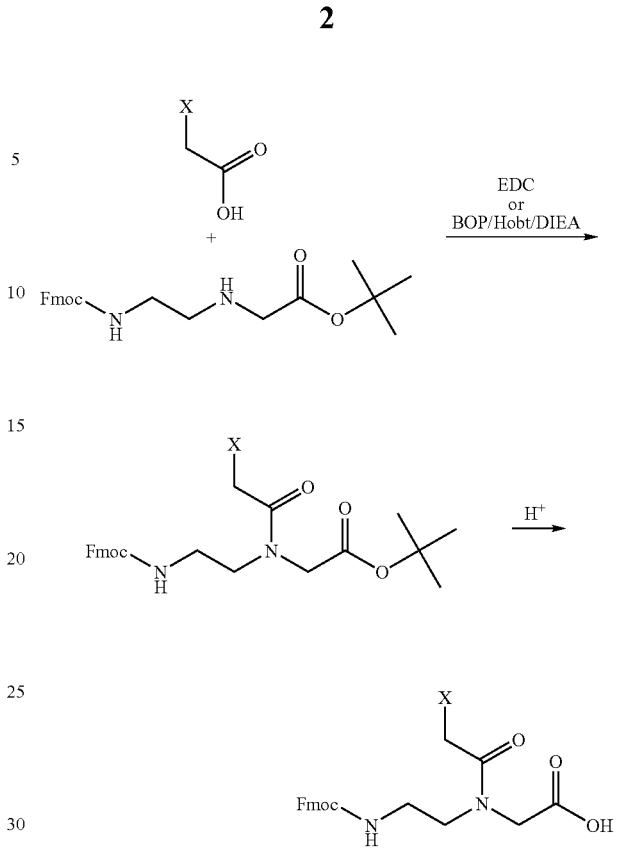

Stephen A. Thompson, John A. Josey, et. al, *Tetrahedron* 1995, 51, 6179–6194.

(X denotes guanine, thymine, cytosine or adenine.)

The first PNA employed the tBoc type PNA monomer unit as described below:

Michael Egholm, Ole Buchardt, Peter E. Nielsen, and Rolf H. Berg
*J. Am. Chem. Soc.* 1992, 114, 1895–1897.

after which a more efficient synthetic method:

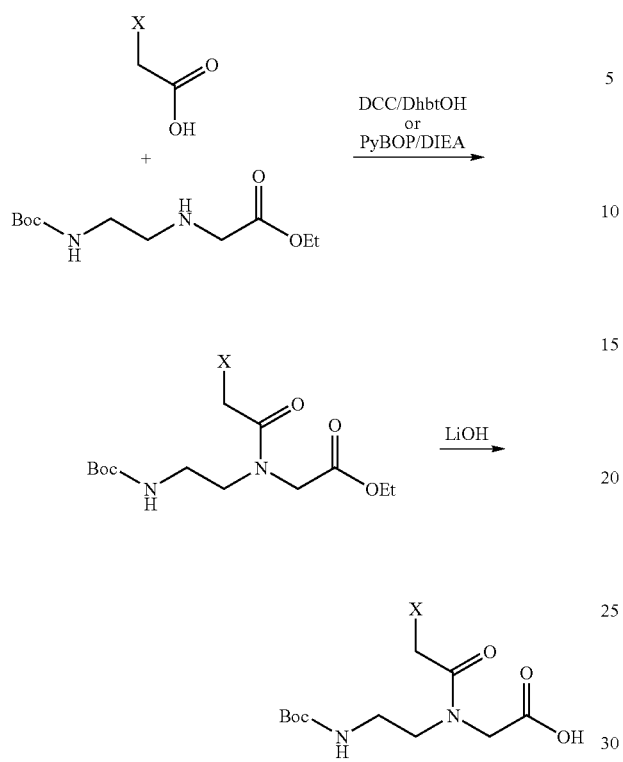

Kim L. Dueholm, Michael Egholm, et. al,
J. Org. Chem. 1994, 59, 5767–5773.

was established.

However, as described above, since the Fmoc type, which is easy to handle, has been developed, the use of the tBoc type is becoming less frequent.

However, when introducing a functional molecule other than the four nucleic acids guanine, thymine, cytosine and adenine, for example, when introducing a photofunctional molecule, since the functional molecule that is to be introduced is often unstable under alkaline conditions, the tBoc type PNA backbone structure, which does not employ alkaline conditions, is very useful. With regard to a "process for producing t-butoxycarbonylaminoethylamines and amino acid derivatives", there is already a patent application filed by the present inventors as Japanese Patent Application No. 2000-268638.

Other than the above process, 5 examples of the synthesis of a monomer unit for a photofunctional PNA oligomer are known. All these cases employ the above-mentioned route, but their yields are either not described or very low (Peter E. Nielsen, Gerald Haaiman, Anne B. Eldrup PCT Int. Appl. (1998) WO 985295 A1 19981126, T. A. Tran, R.-H. Mattern, B. A. Morgan (1999) J. Pept. Res, 53, 134-145, Jesper Lohse et al. (1997) Bioconjugate Chem., 8, 503-509, Hans-georg Batz, Henrik Frydenlund Hansen, et al. PCT Int. Appl. (1998) WO 9837232 A2 19980827, Bruce Armitage, Troels Koch, et al. (1998) Nucleic Acid Res., 26, 715-720, Hans-georg Batz, Henrik Frydenlund Hansen, et al.) Furthermore, since the structures of the compounds used have the characteristic of being comparatively stable under alkaline conditions, it is surmised that, when a chromophore that is unstable under alkaline conditions is present, an efficient synthesis by a method similar to the above-mentioned conventional method, that is to say, route A below, is not possible.

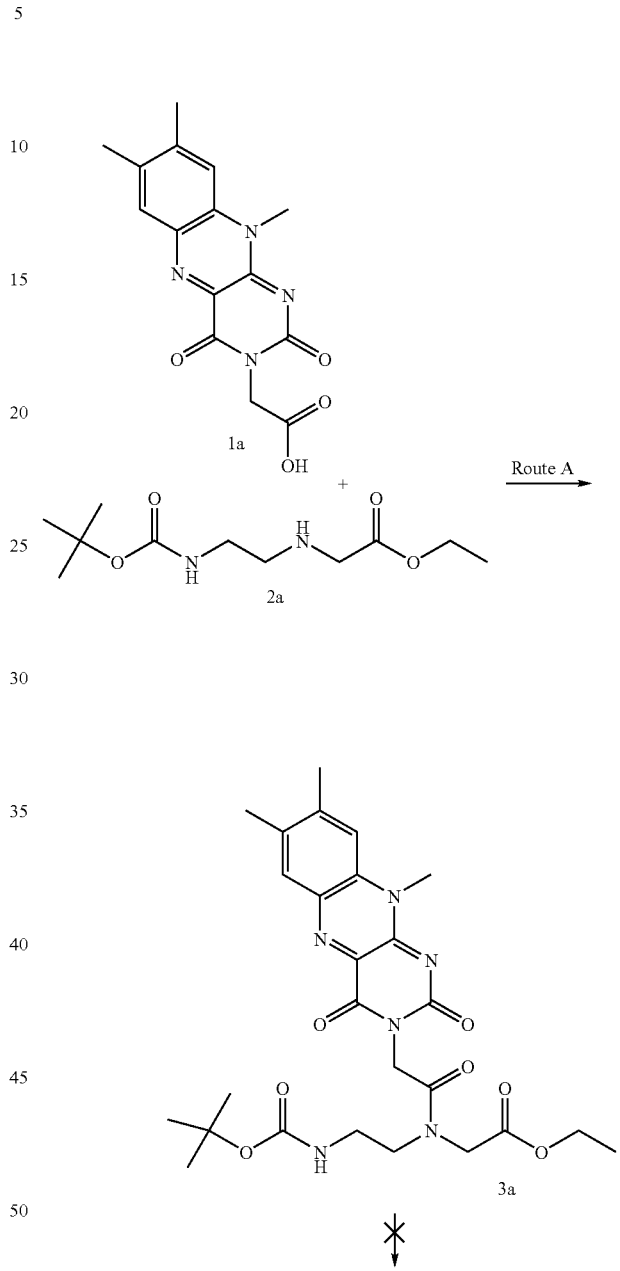

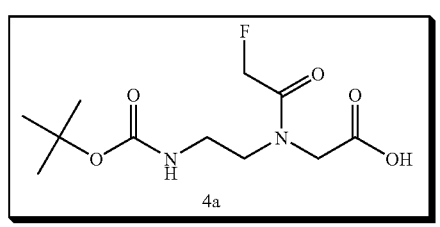

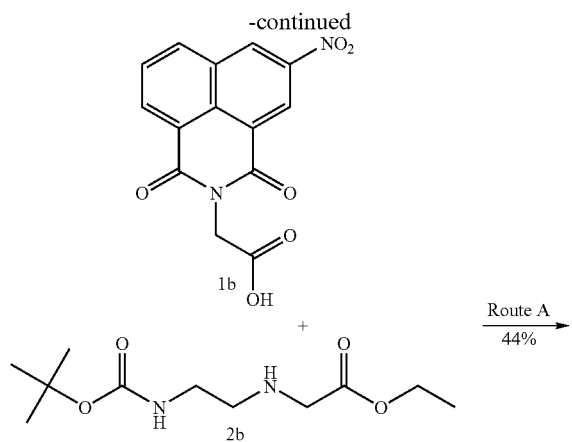

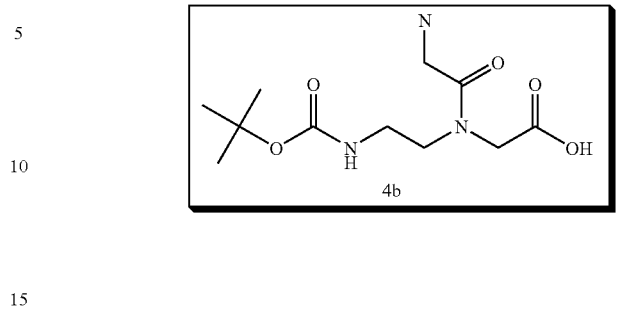

There is therefore a strong desire for the establishment of a technique that functionalises a PNA monomer efficiently as well as for the development of a functional PNA monomer such as, for example, a photofunctional PNA monomer.

DISCLOSURE OF INVENTION

It is an object of the present invention to provide a novel functional PNA monomer and an efficient synthetic method therefor that can eliminate the above-mentioned problems.

As a result of an intensive investigation by the present inventors in order to solve the above-mentioned problems, as shown in route B below, a photofunctional PNA monomer 4 has been synthesised successfully and substantially stoichiometrically using a t-butoxycarbonylaminoethylamine derivative 6 as a PNA backbone structure by condensation with an activated ester derivative 5 containing a pentafluorophenyl group 1.

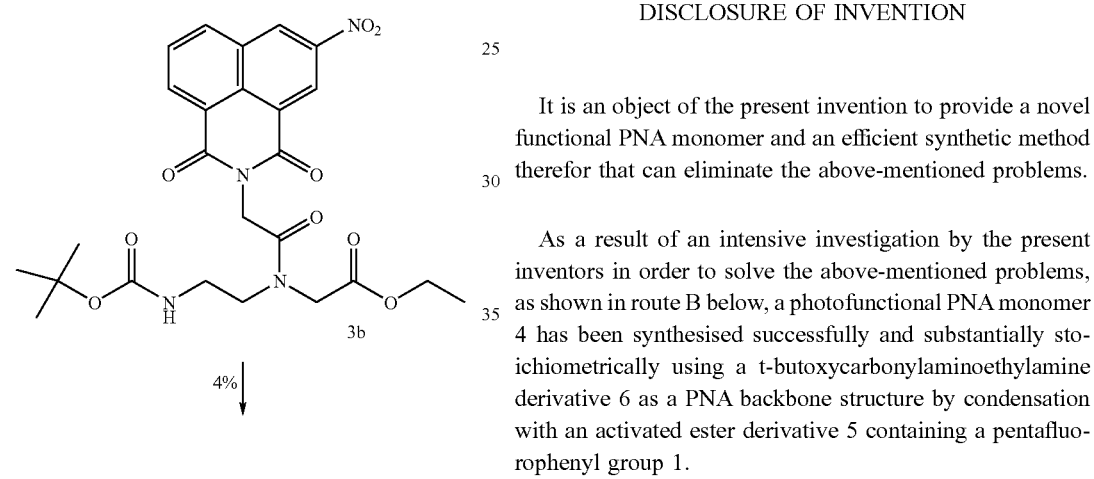

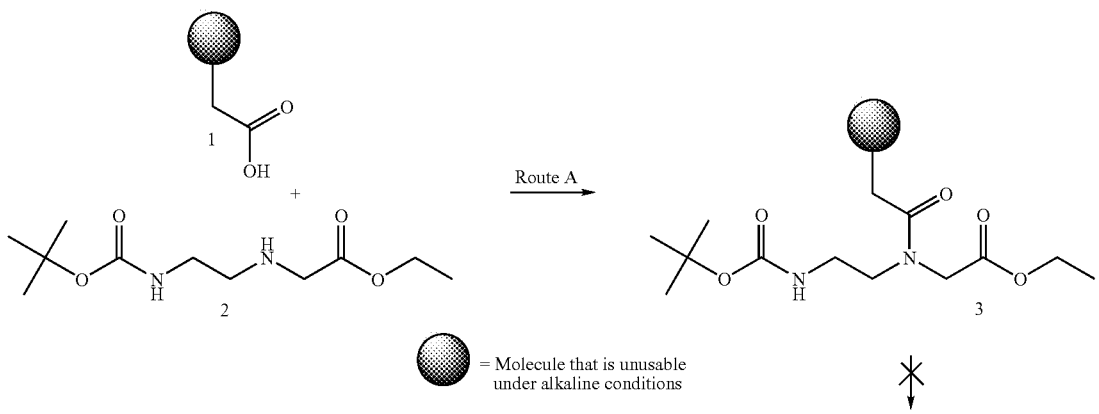

-continued

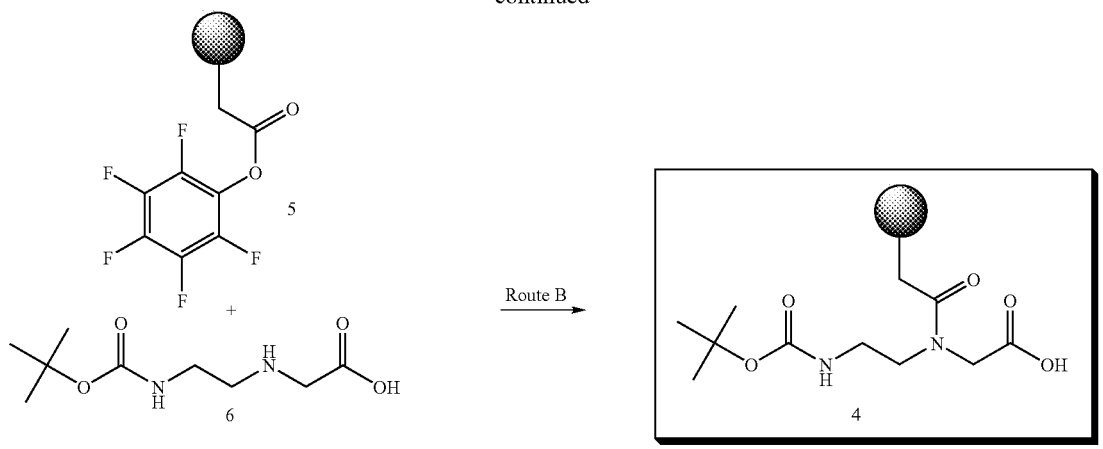

Furthermore, the present inventors have also succeeded in synthesising a photofunctional PNA monomer 4 substantially stoichiometrically using an ω-amino acid derivative 8 as a PNA backbone structure by condensation with an activated ester derivative 7 containing a pentafluorophenyl group 1 as shown in route C below:

That is to say, the present invention relates to a compound represented by general formula (I) below.

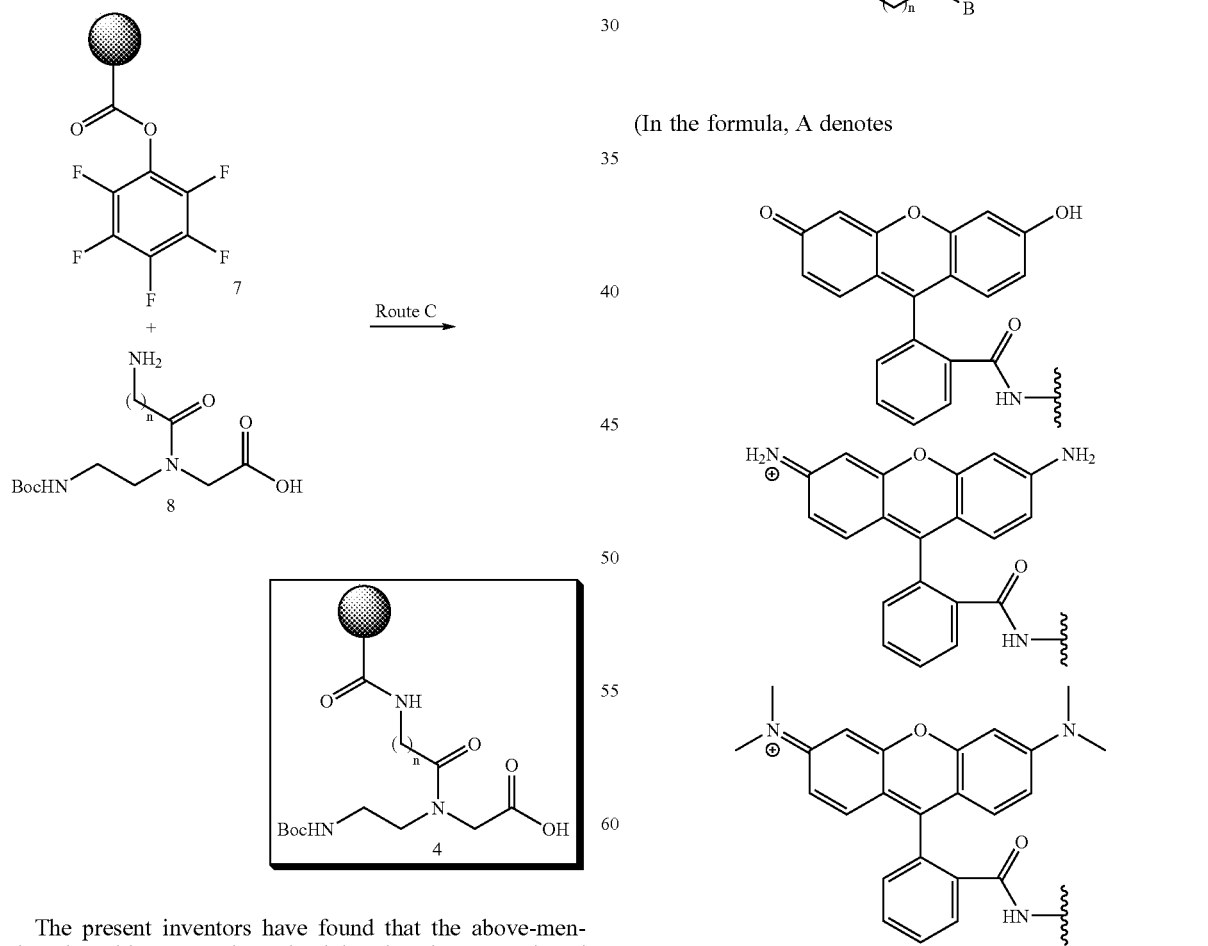

(In the formula, A denotes

The present inventors have found that the above-mentioned problems can be solved by the above-mentioned routes B and C, and the present invention has thus been accomplished.

-continued
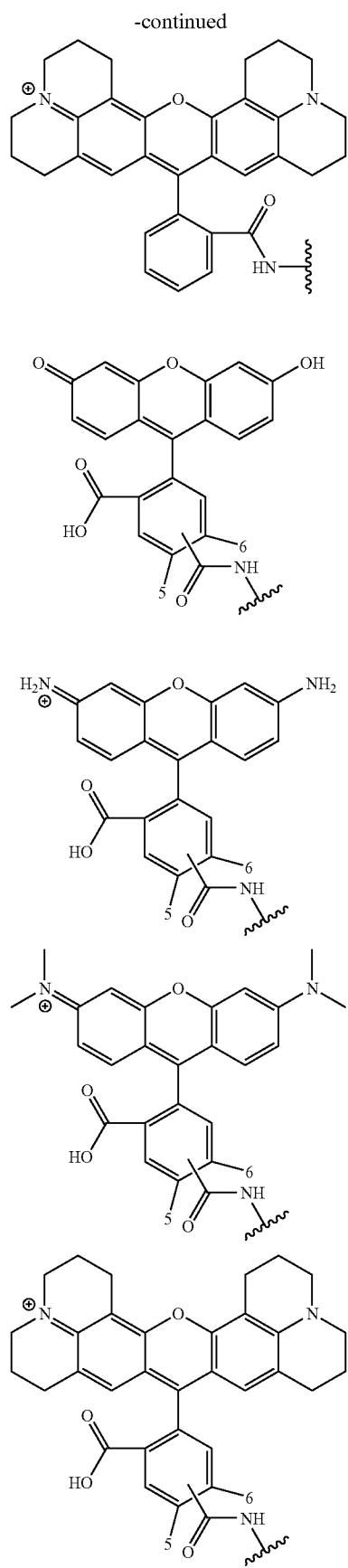
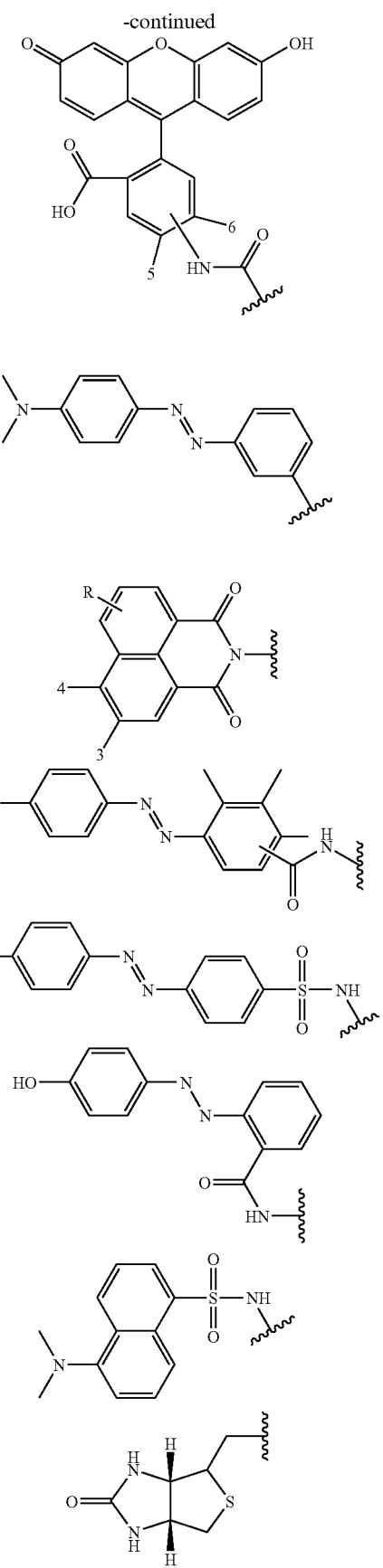

-continued

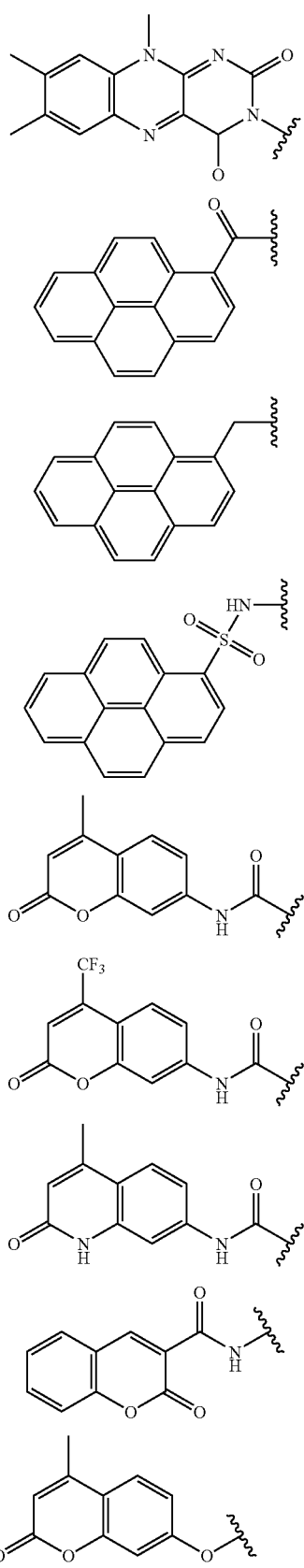

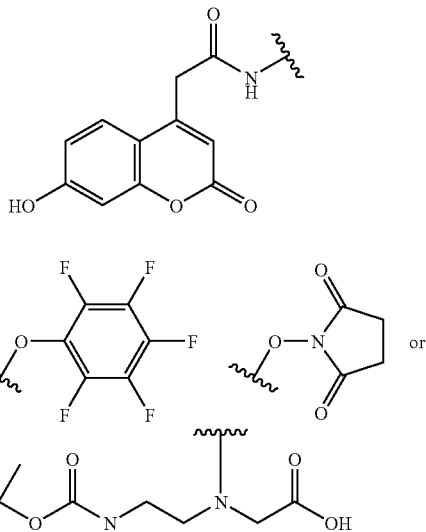

B denotes

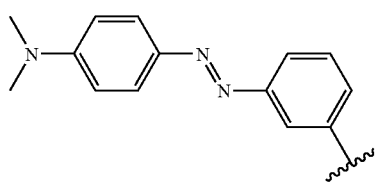

R denotes H, NO$_2$, NH$_2$, NHCbz, Br, F, Cl or SO$_3$Na$_2$, and n is an integer of 1 to 4, wherein when A denotes

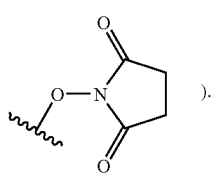

then B denotes

Furthermore, the present invention relates to a process for producing a functional PNA monomer by reacting a t-butoxycarbonylaminoethylamine with a derivative of a functional molecule so as to incorporate the functional molecule into a PNA monomer, characterised in that the derivative of a functional molecule is an activated ester.

Furthermore, the present invention relates to the above-mentioned production process, characterised in that the activated ester has, on the carbonyl carbon forming the ester bond, a group represented by general formula (II) below:

$$A-()_n \sim \quad (II)$$

(In the formula, A denotes
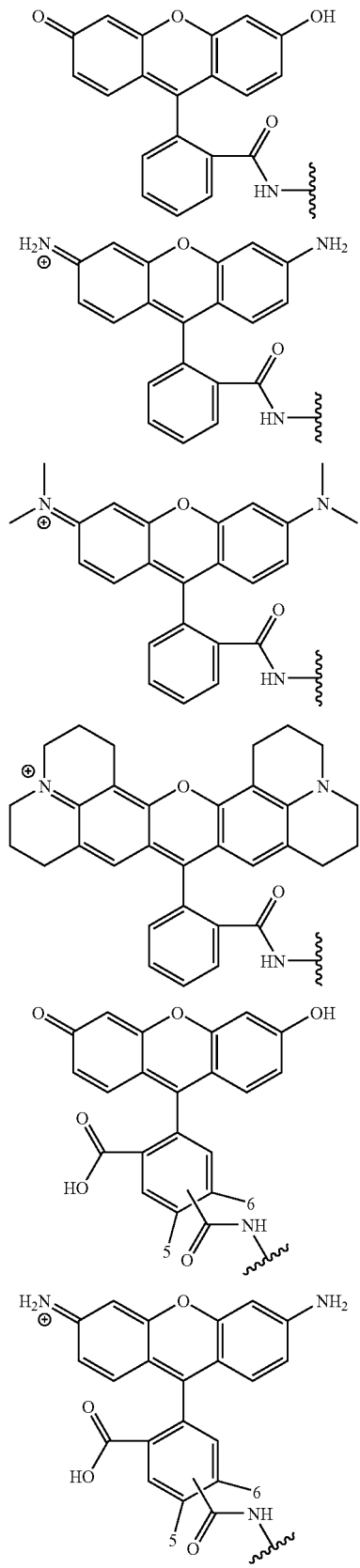
-continued
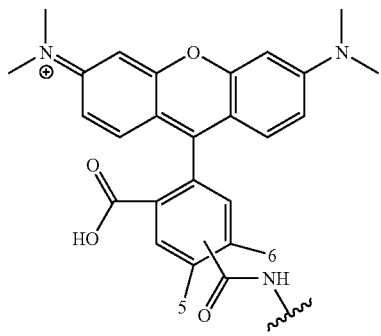
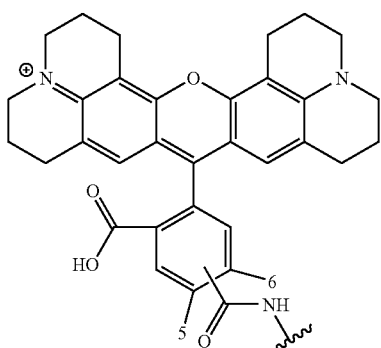
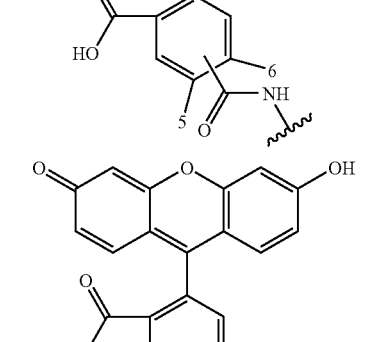
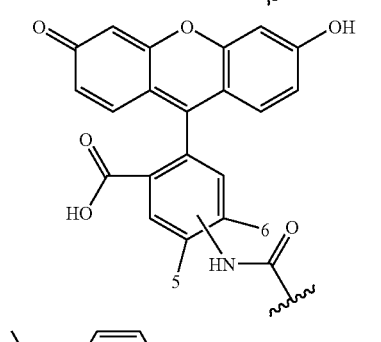
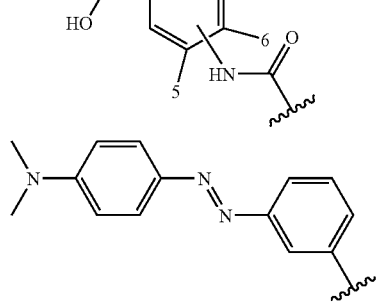
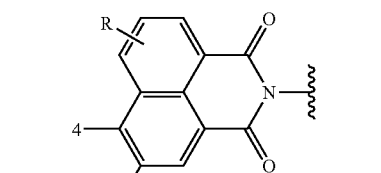
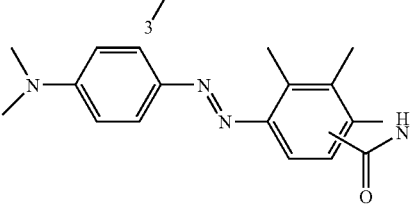
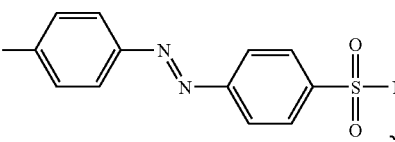

-continued

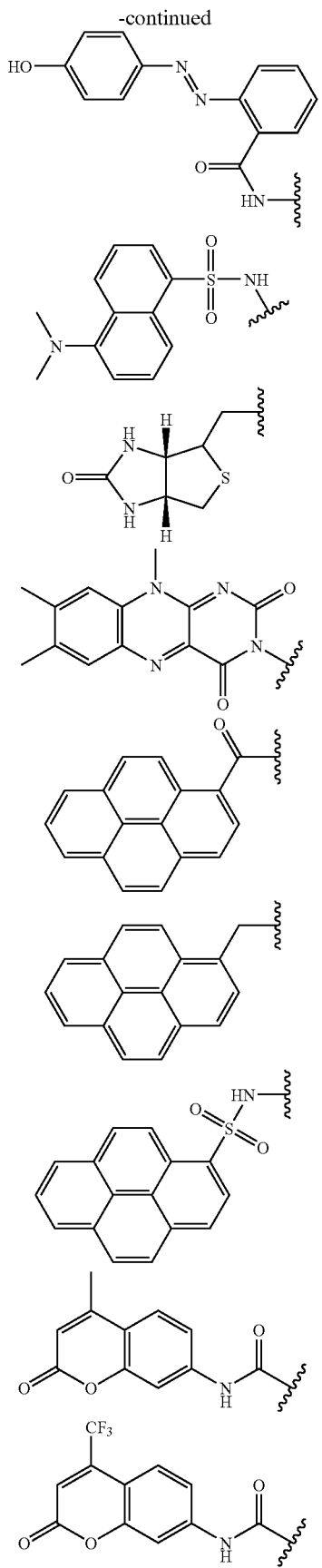

-continued

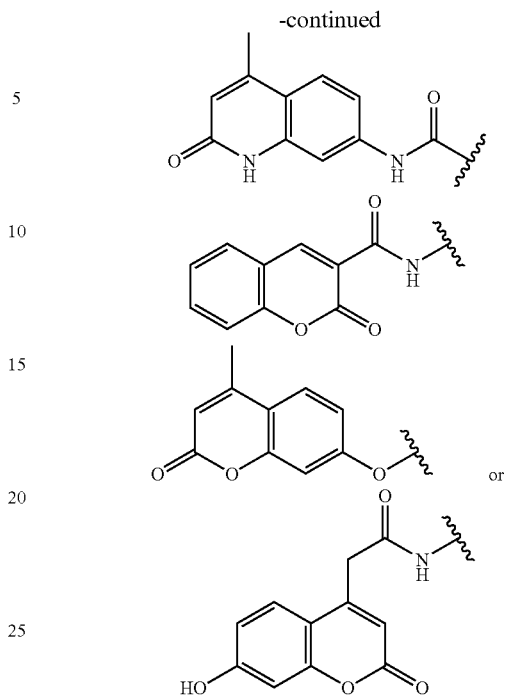

R denotes H, NO$_2$, NH$_2$, NHCbz, Br, F, Cl or SO$_3$Na$_2$, and n is an integer of 1 to 4.).

Furthermore, the present invention relates to the above-mentioned production process, characterised in that the activated ester has, on its carbonyl carbon, a pentafluorophenoxy group or a succinimidoxy group.

Furthermore, the present invention relates to a process for producing an activated ester, characterised in that it includes reacting a carboxylic acid derivative of a functional molecule with a compound having a pentafluorophenoxy group or a succinimidoxy group.

Furthermore, the present invention relates to a process for producing a carboxylic acid derivative of a functional molecule, characterised in that it includes reacting a derivative of the functional molecule with an aliphatic carboxylic acid.

Furthermore, the present invention relates to a process for producing a functional PNA monomer from a functional molecule, including:

producing a derivative of the functional molecule from the functional molecule, producing a carboxylic acid derivative of the functional molecule from the derivative of the functional molecule, producing an activated ester from the carboxylic acid derivative of the functional molecule, and producing a functional PNA monomer from the activated ester, characterised in that it includes one or more of a) to c) below:

a) in the production of the carboxylic acid derivative of the functional molecule, reacting the derivative of the functional molecule with an aliphatic carboxylic acid;

b) in the production of the activated ester, reacting the carboxylic acid derivative of the functional molecule with a compound having a pentafluorophenoxy group or a succinimidoxy group; and c) in the production of the functional PNA monomer, reacting a t-butoxycarbonylaminoethylamine with the activated ester derivative of the functional molecule.

Furthermore, the present invention relates to a process for producing a functional PNA monomer by reacting a derivative of a functional molecule with an ω-amino acid derivative represented by general formula (III) below, thereby incorporating the functional molecule into a PNA monomer, characterised in that the derivative of the functional molecule is an activated ester:

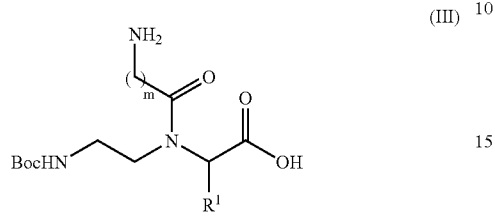
(III)

(In the formula, $R^1$ denotes a hydrogen atom or a straight- or branched-chain $C_1$ to $C_5$ alkyl group, and m denotes an integer of 1 to 11.).

Furthermore, the present invention relates to the above-mentioned production process, characterised in that the activated ester has, on its carbonyl group forming an ester bond, a group represented by general formula (II) below, either directly or via an aliphatic chain or a peptide chain:

(II)

(In the formula, A denotes

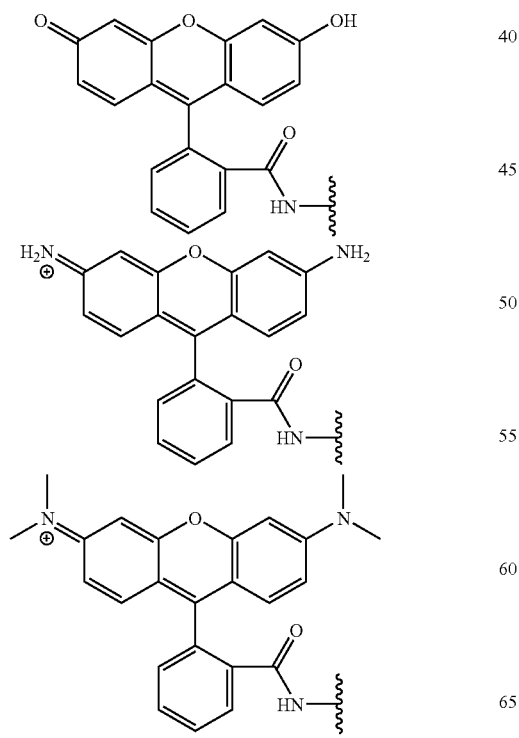

-continued

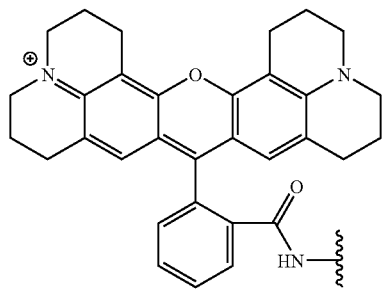

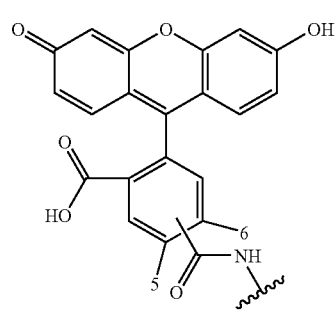

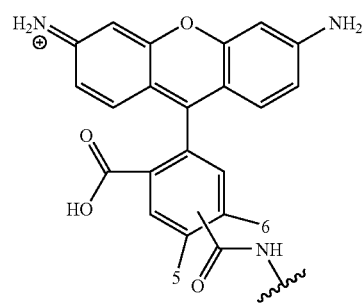

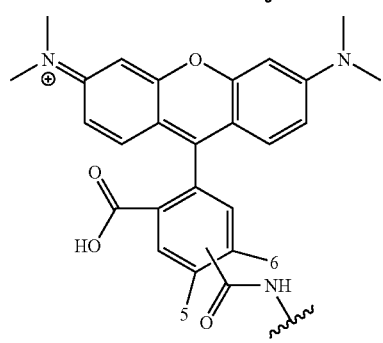

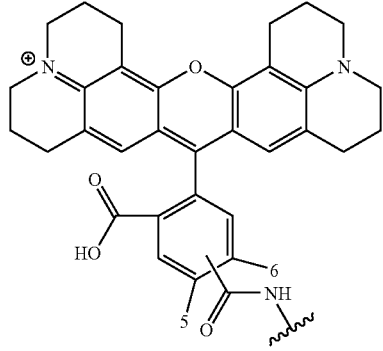

-continued
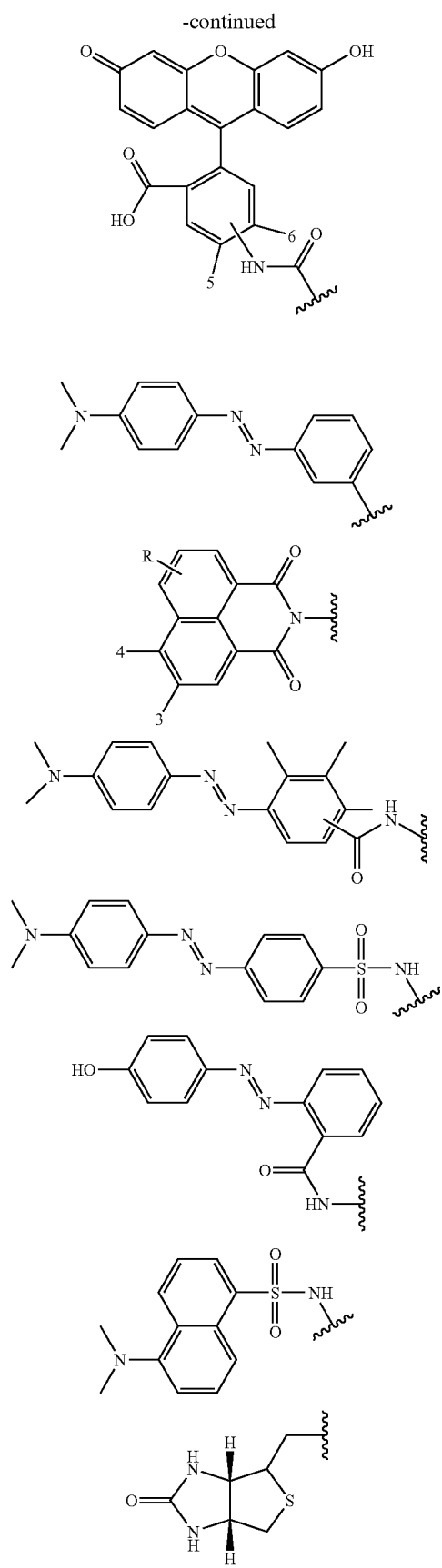
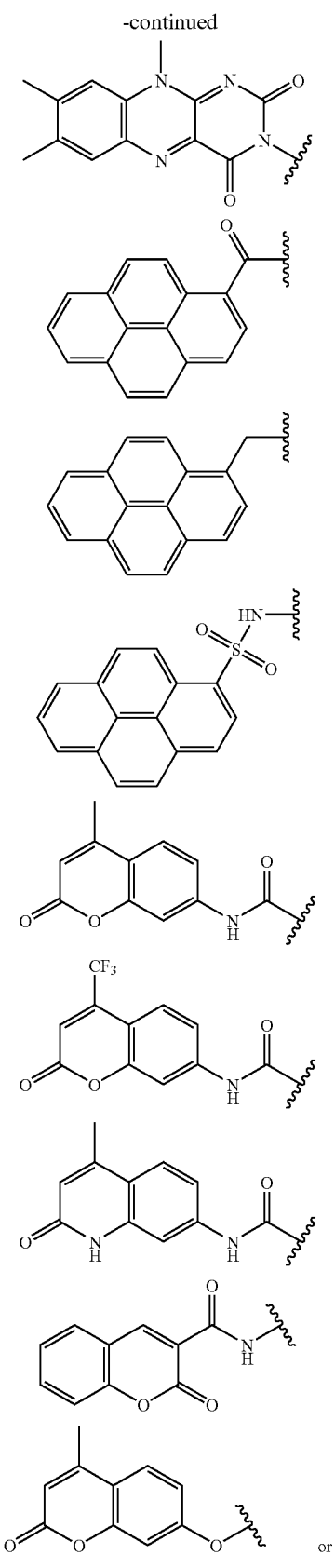
or

-continued

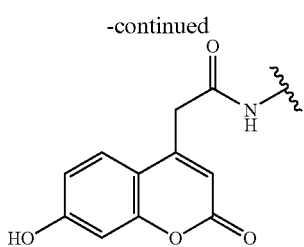

R denotes H, NO$_2$, NH$_2$, NHCbz, Br, F, Cl or SO$_3$Na$_2$, and n is an integer of 1 to 4:).

Furthermore, the present invention relates to the above-mentioned production process, characterised in that the activated ester has, on its carbonyl carbon, a pentafluorophenoxy group or a succinimidoxy group.

Furthermore, the present invention relates to a process for producing a functional PNA monomer from a functional molecule, including producing an activated ester from the functional molecule and producing a functional PNA monomer from the activated ester, characterised in that the production of the activated ester from the functional molecule includes reacting m-methyl red with a compound that contains a succinimidoxy group, and/or the production of the functional PNA monomer from the activated ester includes reacting a benzyloxycarbonyl-ω-amino acid derivative represented by general formula (III) with the activated ester derivative of the functional molecule, thereby incorporating the functional molecule into a PNA monomer.

Features of the present invention are now explained in detail by comparing the processes of the present invention with the conventional processes.

The synthesis of tBoc type PNA monomer unit 4 usually employs route A below:

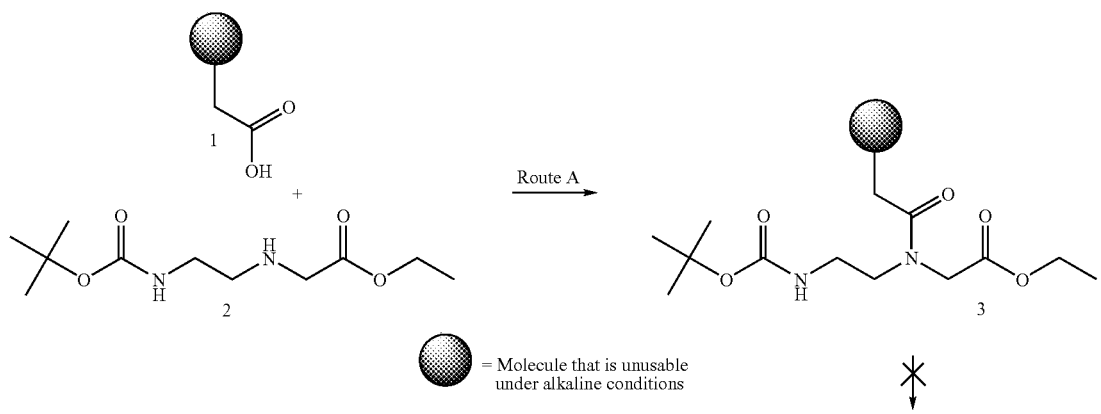

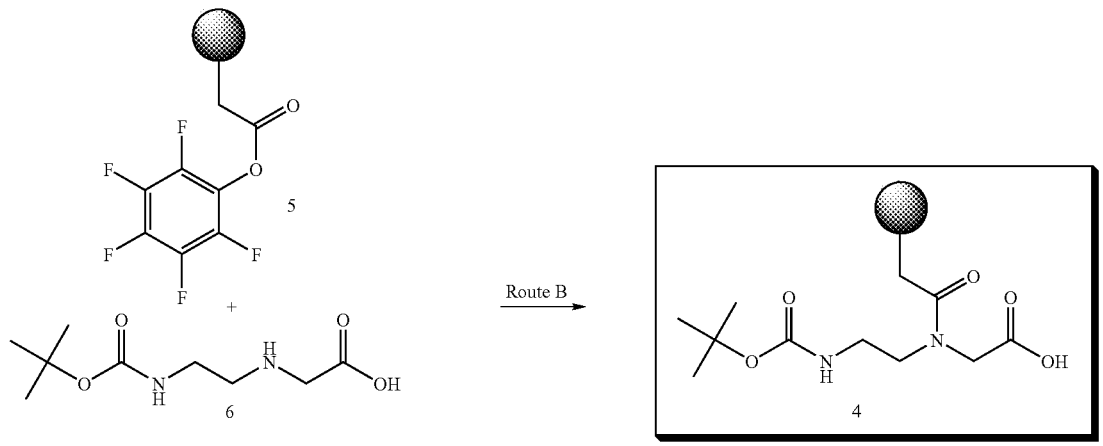

That is to say, it is a process in which, after synthesising 3 by dehydration condensation between 1 and 2, 3 is subjected to alkaline hydrolysis to give 4. This process is also used when introducing the four nucleic acid base groups guanine, thymine, cytosine, and adenine. When introducing a functional molecule (this refers to a known compound cited in Table 1) other than the above-mentioned groups, route A is also employed. However, since many photofunctional molecules are generally unstable under alkaline conditions, it is impossible to obtain 4 efficiently by route A. Instead of using the conventional PNA backbone structure 2, the condensation is therefore carried out using 6 obtained by the prior hydrolysis of 2. Since 6 includes a free carboxylic acid group, as is the case for 1, there is a possibility that an intramolecular dehydration condensation might occur, and a direct dehydration condensation using a condensing agent such as DCC cannot therefore be employed. The reaction is therefore devised so that the free carboxylic acid group and secondary amino group of 6 do not condense intramolecularly with each other by converting 1 into an activated ester derivative 5 using pentafluorophenol and then reacting 5 with 6 (route B). This gives 4 stoichiometrically. As hereinbefore described, there is no precedent for the process of synthesising 4 by converting a photofunctional molecule into its activated ester and then reacting it with 6, and it can be said that this process will hereafter be an indispensable technique for the synthesis of a variety of photofunctional PNA monomers.

Since benzyloxycarbonyl-ω-amino acid derivatives represented by general formula (III) below, which are used in route C, already have a linker (carboxylamino acid):

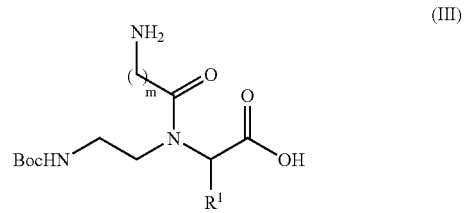

(III)

(in the formula, $R^1$ denotes a hydrogen atom or a straight- or branched-chain $C_1$ to $C_5$ alkyl group, and m denotes an integer of 1 to 11), the derivatives are very versatile, and reaction of the derivatives with an activated ester derivative gives a target functional PNA monomer unit in one step. Moreover, many commercially available benzyloxycarbonyl-ω-amino acid derivatives can be used. The route C is therefore particularly effective when targeting a comparatively expensive photofunctional molecule.

On the other hand, incorporation of a photofunctional molecule such as a sulphonyl chloride type or the highly sterically hindered methyl red into a PNA monomer can be carried out desirably by route B.

It is therefore possible to synthesise a variety of functional PNA monomers by appropriately choosing one from the synthetic method via route B and that via route C of the present invention.

In accordance with the present invention, photofunctional monomer units such as a Naphthalimide type, a Flavin type, a Dabcyl type, a Biotin type, an FAM type, a Rhodamine type, a TAMRA type, an ROX type, an HABA type, a Pyrene type and a Coumarin type can be obtained. It is also possible to obtain photofunctional monomer units other than the above-mentioned types and to obtain functional monomer units other than the photofunctional monomer units.

MODES FOR CARRYING OUT THE INVENTION

Figure 1:
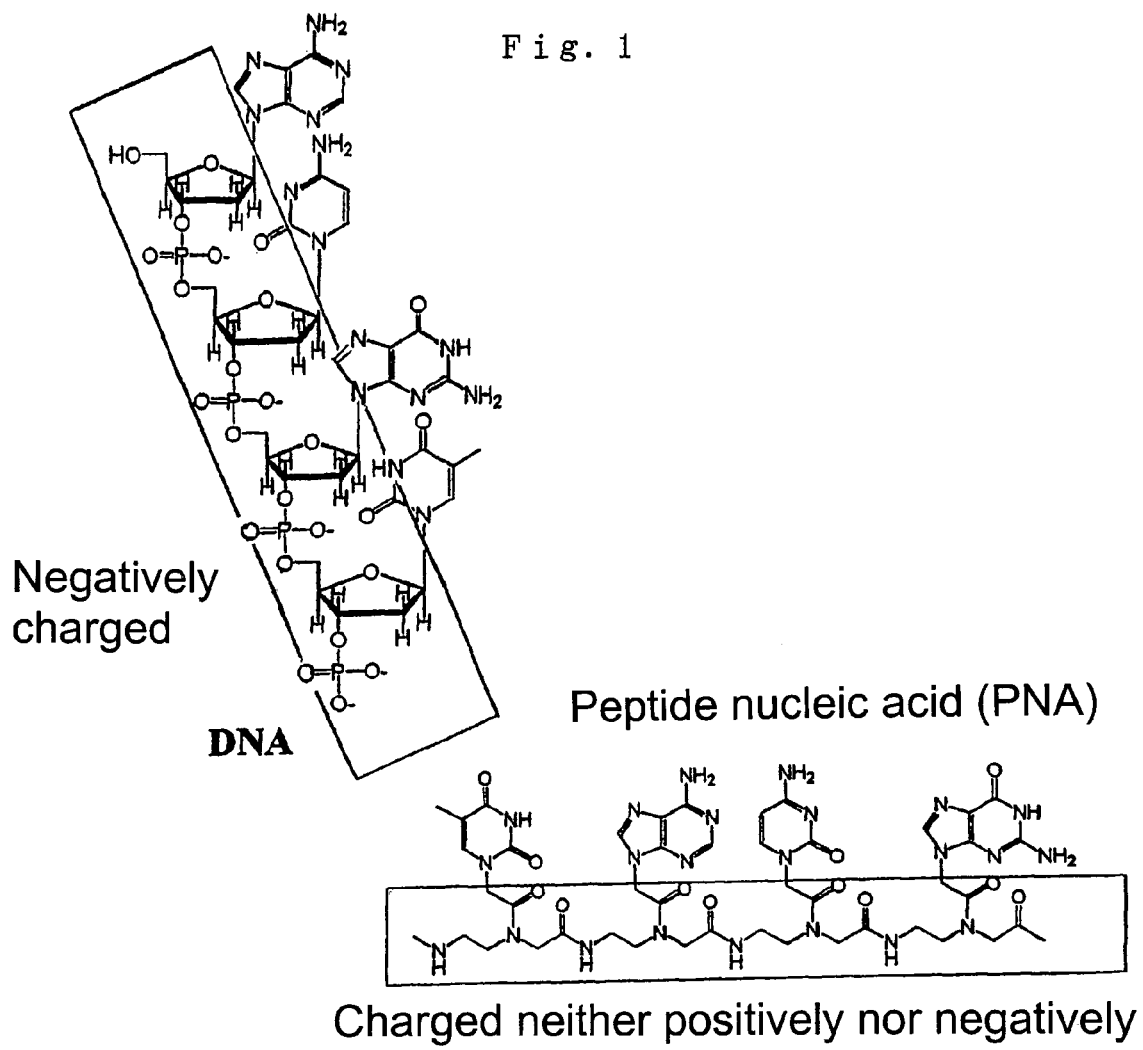
FIG. 1 is a diagram showing differences in the structure and the electrical charge between DNA and PNA.
Figure 2:
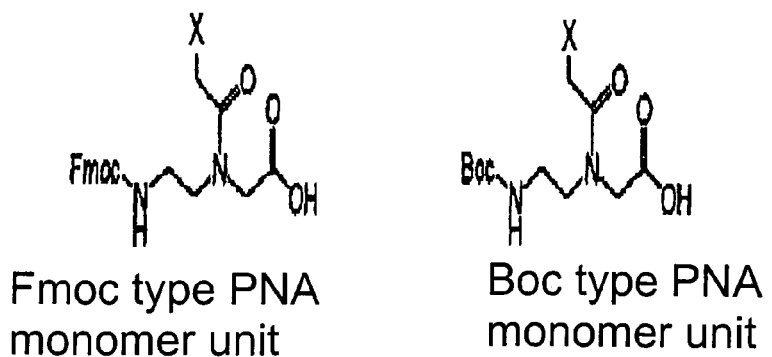
FIG. 2 is a diagram showing the structures of two types of PNA monomer unit.

Conventionally, in the synthesis of a photofunctional monomer unit, for example, in the synthesis of compound 4a,

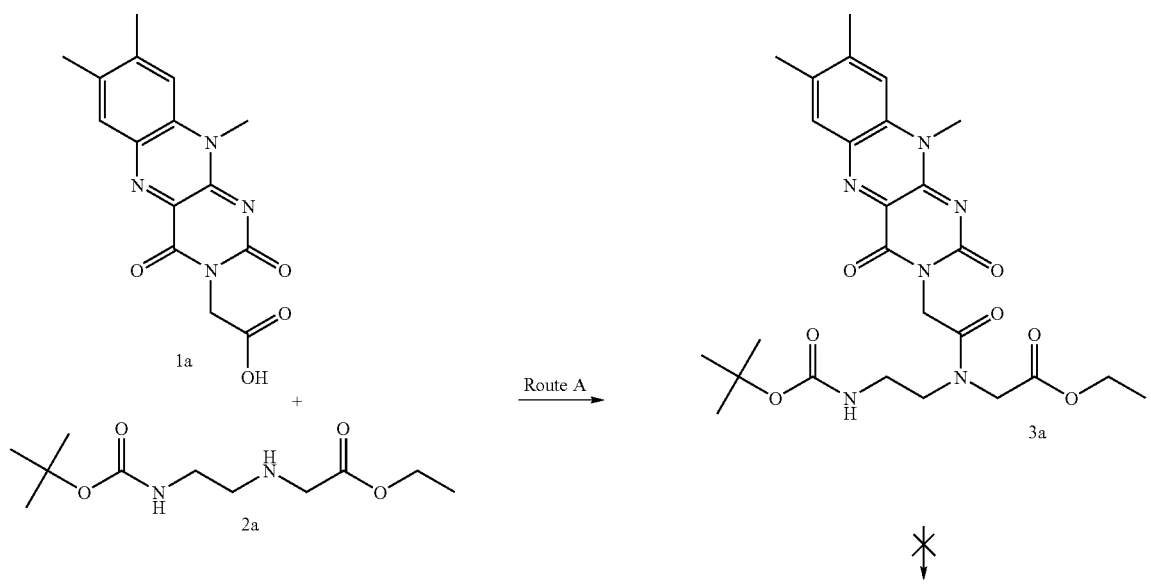

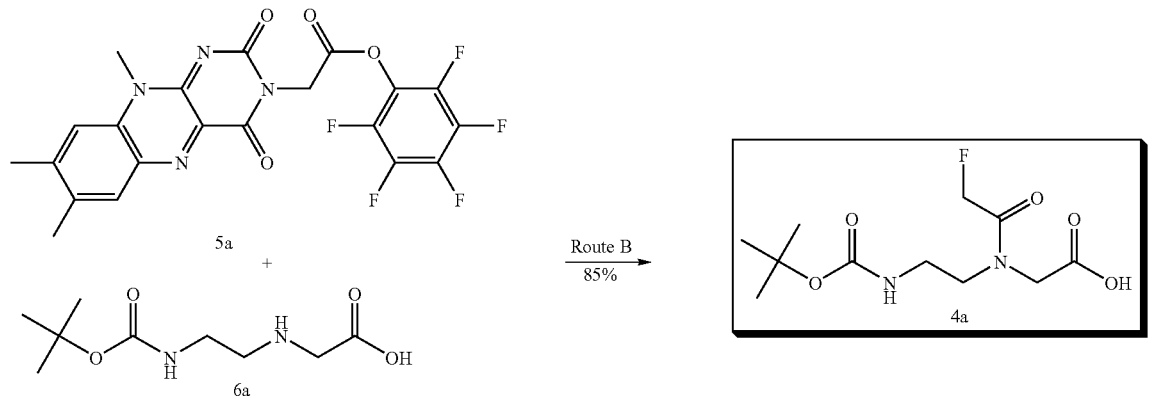

a carboxylic acid derivative 1a of a functional molecule and a PNA backbone structure 2a are subjected to dehydration condensation to give 3a, which is then subjected to alkaline hydrolysis to give the target 4a (route A). Although the flavin skeleton of 1a is stable towards acid, it is easily decomposed under alkaline conditions to give 6,7-dimethylquinoxalinedione, and it is therefore impossible to obtain 4a efficiently even when 3a can be synthesised. When 1a is converted into an activated ester derivative 5a and then reacted with 6a, the reaction proceeds substantially stoichiometrically to give 4a with a yield of 85% (route B).

In the synthesis of compound 4b,

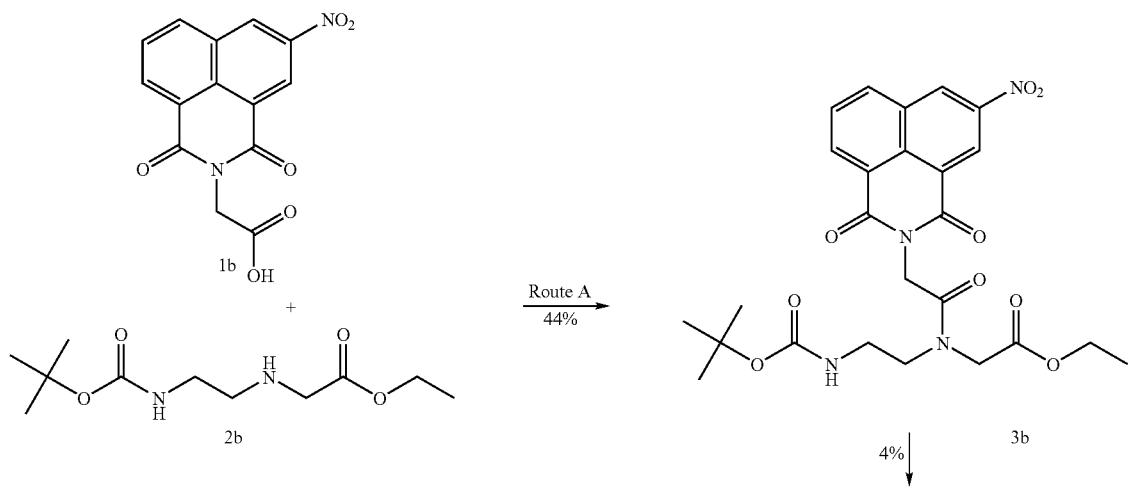

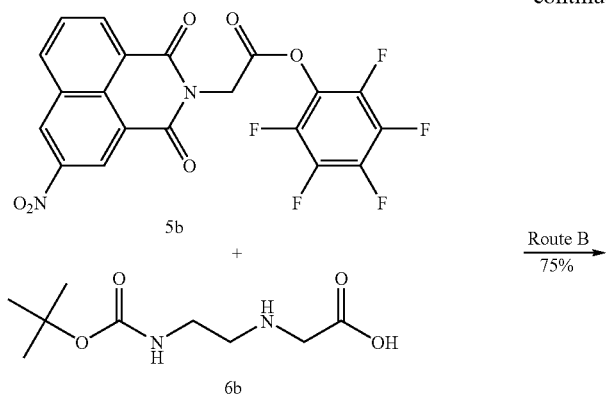

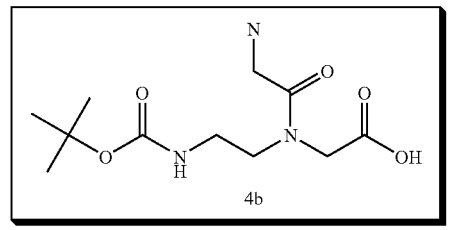

although a naphthalimide derivative 3b is obtained from the corresponding 1b and 2b with a yield of 44% the subsequent alkaline hydrolysis gives 4b in only 4% (route A). When 1b is converted into activated ester derivative 5b and then reacted with 6b, the reaction proceeds to give 4b with a yield of 75% (route B).

The production of 1a and 1b, which are carboxylic acid derivatives, is carried out using an aliphatic carboxylic acid, and preferable a straight-chain aliphatic carboxylic acid.

In the production of a monomer that is incorporated at a terminal amino group of a PNA, an activated ester having a succinimide group can preferably be used.

As the ω-amino acid derivative represented by general formula (III) that is used in route C, one having a $C_1$ to $C_{11}$ carbon chain on the carbonyl carbon of its amino acid moiety can be used, but since a PNA is generally expected to be a hybrid with DNA, it is desirable for the derivative to be similar sterically to DNA. Taking this point into consideration, when a carboxylamino acid is used as a linker, one having Z-glycine as an amino moiety is the most suitable.

With regard to the method for synthesising a photofunctional PNA oligomer, the Fmoc method and the tBoc method can be used. The Fmoc method involves a protecting group removal step using an alkaline reagent, and its use is inappropriate when designing a photofunctional PNA oligomer. On the other hand, since the tBoc method does not employ alkaline conditions in its synthetic steps, it is suitable as a synthetic method for a photofunctional PNA oligomer. Application of the PNA monomer related to the present invention to the tBoc method therefore allows a photofunctional PNA oligomer to be synthesised efficiently.

EXAMPLES

The present invention is explained below in more detail by way of examples, but the present invention is in no way limited thereby.

Example 1

Synthesis of 2,3,4,5,6-pentafluorophenyl 2-(5,7,8trimethyl-1,3-dioxo-2,5-dihydro-2,4-diazaphenazin-2-yl)acetate (5a)

EDC (73.2 mg, 382 μmol) was added to a DMF solution (10 ml) of 1a (100 mg, 318 μmol) and PfpOH (70.2 mg, 381 μmol) at 0° C., and this reaction mixture was stirred at 0° C. for 1 hour and at room temperature for 12 hours. This reaction mixture was concentrated under reduced pressure, and the residue was subjected to partition extraction with a water-chloroform system. The organic layer was dried with magnesium sulphate and concentrated under reduced pressure, and the residue was then purified by silica gel column chromatography (2.5% MeOH/CHCl$_3$) to give 5a (130 mg, 85%). $^1$H NMR (CDCl$_3$) δ 8.07 (s, 1H), 7.44 (s, 1H), 5.21 (s, 2H), 4.14 (s, 3H), 2.55 (s, 3H), 2.45 (s, 3H); HRMS (FAB$^+$, NBA/CH$_2$Cl$_2$) C$_{21}$H$_{14}$O$_4$N$_4$F$_5$ [(M+H)$^+$] Calcd. 481.0934, Exp. 481.0950; UV λmax (DMF) 390, 460 (nm).

Example 2

Synthesis of 2-(N-(2-((t-butoxy)carbonylamino) ethyl))-2-(5,7,8-trimethyl-1,3-dioxo (2,5-dihydro-2, 4-diazaphenazin-2yl)acetylamino)acetic acid (4a)

Diisopropylethylamine (36.3 μL, 208 μmol) was added to a DMF solution (10 mL) of 5a (100 mg, 208 μmol) and 6 (45.4 mg, 208 μmol) and stirred at room temperature for 15 hours. This was concentrated under reduced pressure, and the residue was purified by silica gel column chromatography (10-50% MeOH/CHCl$_3$) to give 4a (130 mg, 85%). $^1$H NMR (CD$_3$OD) δ 7.94 (s) and 7:86 (s) (1H), 7.80 (s) and 7.75 (s) (1H), 5.03 (s) and 4.88 (s) (2H), 4.17 (s) and 4.13 (s) (3H), 3.64 and 3.52 (2H), 3.38 and 3.26 (2H), 2.58 (s) and 2.56 (s) (3H), 2.46 (s) and 2.44 (s) (3H), 1.46 (s) and 1.41 (s) (9H); HRMS (FAB$^+$, NBA/CH$_2$Cl$_2$) C$_{24}$H$_{31}$O$_7$N$_6$[(M+H)$^+$] Calcd. 515.2252, Exp. 515.2273; UV λmax (DMF) 390, 460 (nm).

Example 3

Synthesis of N-(4-dimethylaminoazobenzene-2'-carbonyl)glycine (1c)

Triethylamine (732 μL, 5.25 mmol) was added to a DMF solution (10 mL) of methyl red (1.35 g, 5 mmol) and t-butylglycine hydrochloride (880 mg, 5.25 mmol), while ice cooling DCC (1.13g, 5.5 mmol) was added thereto and this was stirred for 30 minutes and further at room temperature for 15 hours. The reaction mixture was filtered, the filtrate was concentrated under reduced pressure, and the residue was purified by silica gel column chromatography (0-10% acetone/CH$_2$Cl$_2$) to give the t-butyl ester derivative (1.05 g, 55%) of 1c as orange needle-shaped crystals. This derivative (765 mg, 2 mmol) was added to formic acid (50 mL), stirred at room temperature for 2 days, and concentrated under reduced pressure to remove the formic acid, and the residue was purified by silica gel column chromatography (0-5% acetone/CH$_2$Cl$_2$) to give 1c (549 mg, 84%) as red needle-shaped crystals. $^1$H NMR (CDCl$_3$) δ 9.99 (brt, 1H), 8.40 (d, J=8 Hz, 1H), 7.89 (d, J=9 Hz, 2H), 7.84 (d, J=8 Hz, 1H), 7.56 (t, J=8 Hz, 1H), 7.49 (t, J=8 Hz, 1H), 6.75 (d, J=9 Hz, 2H), 4.42 (d, J=5 Hz, 2H), 3.10 (s, 6H); $^{13}$C NMR (CDCl$_3$) δ 167.61; 153.39, 150.86, 143.30, 132.49, 131.47, 129.38, 127.69, 126.28, 116.24, 111.63, 43.20, 40.24;

Example 4

Synthesis of 2,3,4,5,6-pentafluorophenyl N-(4-dimethylaminoazobenzene-2'-carbonyl)glycinate (5c)

DCC (308 mg, 1.5 mmol) was added to a DMF solution (10 mL) of 1c (326 mg, 1 mmol) and PfpOH(276 mg, 1.5 mmol) while ice cooling, and this reaction mixture was stirred at room temperature for 15 hours. The reaction mixture was filtered, the filtrate was concentrated under reduced pressure, and the residue was purified by silica gel column chromatography (0-5% acetone/CH$_2$Cl$_2$) to give 5c (449 mg, 91%) as an orange powder. 1H NMR (CDCl$_3$) δ 10.14 (brt, 1H), 8.37 (d, J=8 Hz, 1H), 7.78 (d, J=9 Hz, 2H), 7.76 (d, J=8 Hz, 1H), 7.57 (t, J=8 Hz, 1H), 7.50 (t, J=8 Hz, 1H), 6.74 (d, J=9 Hz, 2H), 4.68 (d, J=5 Hz, 2H) 3.06 (s, 6H).

Example 5

Synthesis of 2-(N-(2-((t-butoxy)carbonylamino)ethyl)-2-(4-dimethylaminoazobenzene-2'-carbonylamino)acetylamino)acetic acid (4c)

Diisopropylethylamine (85 μL, 0.5 mmol) was added to a DMF solution (5 mL) of 5c (246 mg, 0.5 mmol) and 6 (109 mg, 0.5 mmol) and stirred at room temperature for 15 hours. This was concentrated under reduced pressure and the residue was purified by silica gel column chromatography (0-30% MeOH/CH$_2$Cl$_2$) to give 4c (225 mg, 72%). $^1$H NMR (CDCl$_3$) δ 9.99 (s) and 9.85 (s) (1H), 8.3-7.6 (m, 4H), 7.4-7.2 (m, 2H), 6.67 (s) and 6.59 (s) (2H), 5.62 (s) and 5.27 (s) (1H), 4.35 (s) and 4.20 (s) (2H), 3.99 and 3.90 (2H), 3.5 (brs) and 3.3 (brs) (2H), 3.2 (brs) and 3.0 (brs) (2H), 2.99 (s) and 2.87 (s) (6H), 1.25 (brs, 9H).

The route from 1c to 4c was as follows:

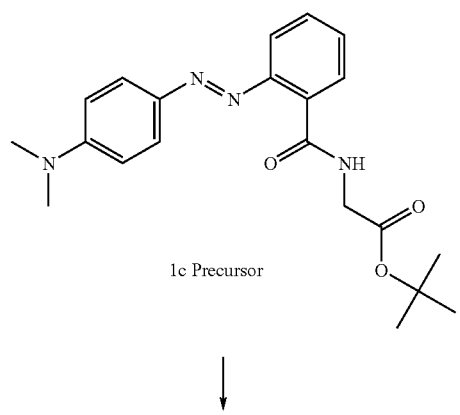

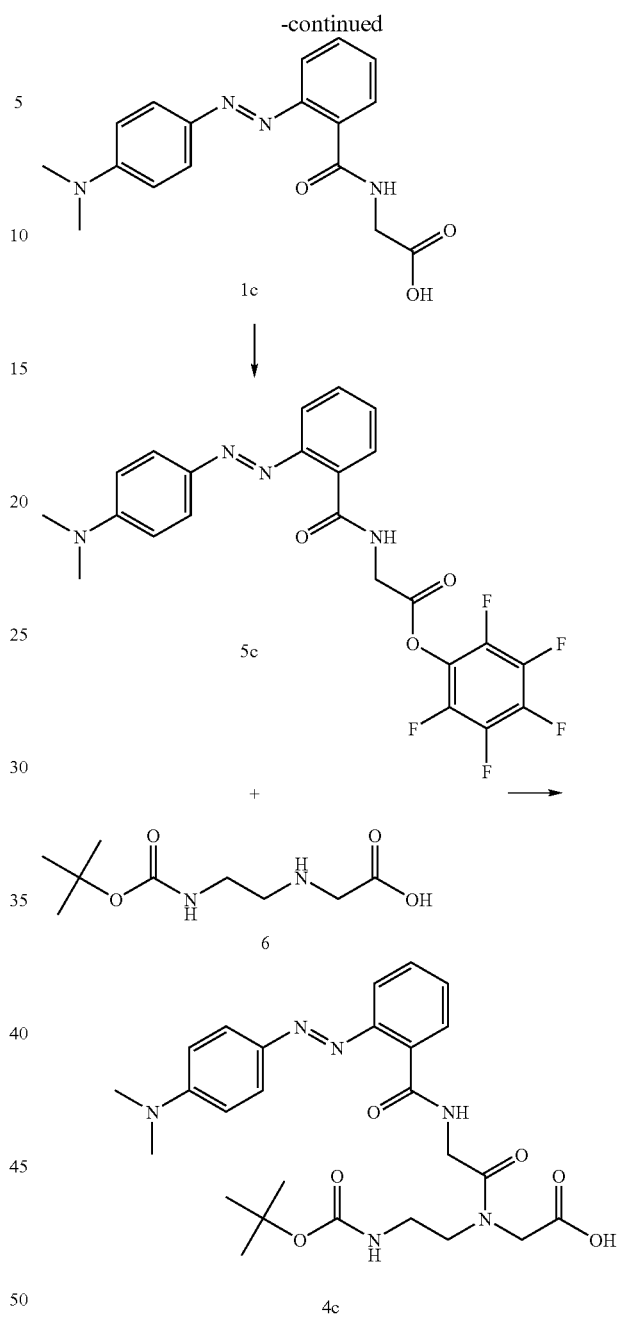

Example 6

Synthesis of N-(4-hydroxyazobenzene-2'-carbonyl)glycine (1d)

Triethylamine (732 μL, 5.25 mmol) was added to a DMF solution (10 mL) of HABA (1.21 g, 5 mmol) and t-butylglycine hydrochloride (880 mg, 5.25 mmol), while ice cooling DCC (1.13 g, 5.5 mmol) was then added and this was stirred for 30 minutes and further at room temperature for 15 hours. The reaction mixture was filtered, the filtrate was concentrated under reduced pressure, and the residue was purified by silica gel column chromatography (0-5% acetone/CH$_2$Cl$_2$) to give the t-butyl ester derivative (1.73 g, 97%) of 1d as an orange powder. This (1.07 g, 3 mmol) was added to formic acid (50 mL), stirred at room temperature for 2 days, and concentrated under reduced pressure to remove the formic acid, and the residue was purified by silica gel column chromatography (0-5% acetone/$CH_2Cl_2$) to give 1d (0.89 g, 99%) as an orange powder. $^1$H NMR ($CDCl_3$) δ 10.45 (brt, 1H), 8.88 (brt, J=5 Hz, 1H), 7.91 (d, J=9 Hz, 2H), 7.85 (d, J=8 Hz, 1H), 7.70 (d, J=8 Hz, 1H), 7.60 (t, J=8 Hz, 1H), 7.57 (t, J=8 Hz, 1H), 6.94 (d, J=9 Hz, 2H), 4.05 (d, J=5 Hz, 2H); $^{13}$C NMR ($CDCl_3$) δ 171.18, 166.44, 161.54, 149.13, 145.34, 133.20, 131.09, 130.18, 129.61, 125.86, 116.00, 115.88, 41.60.

Example 7

Synthesis of 2,3,4,5,6-pentafluorophenyl N-(4-hydroxyazobenzene-2'-carbonyl)glycinate (5d)

DCC (308 mg, 1.5 mmol) was added to a DMF solution (10 mL) of 1d (299 mg, 1 mmol) and PfpOH (276 mg, 1.5 mmol) while ice cooling, and this reaction mixture was stirred at room temperature for 15 hours. The reaction mixture was filtered, the filtrate was concentrated under reduced pressure, and the residue was purified by silica gel column chromatography (0-5% acetone/$CH_2Cl_2$) to give 5d (46 mg, 10%) as an orange powder. $^1$H NMR ($CDCl_3$) δ 9.67 (brs, 1H), 9.02 (brt, 1H), 7.8-7.7 (m, 3H), 7.6-7.5 (m, 2H) 7.23 (d, J=9 Hz, 1H), 6.86 (d, J=9 Hz, 2H), 4.67 (d, J=5 Hz, 2H).

Example 8

Synthesis of 2-(N-(2-((t-butoxy)carbonylamino) ethyl)-2-(4hydroxyazobenzene-2'-carbonylamino) acetylamino)acetic acid (4d)

Diisopropylethylamine (14 μL, 80 μmol) was added to a DMF solution (5 mL) of 5d (37 mg, 80 μmol) and 6 (18 mg, 80 μmol) and stirred at room temperature for 15 hours. This was concentrated under reduced pressure, and the residue was purified by silica gel column chromatography (0-30% MeOH/$CH_2Cl_2$) to give 4d (13 mg, 33%). $^1$H NMR ($CDCl_3$) δ 9.77 (s) and 9.59 (s) (1H), 8.26 (s) and 8.14 (s) (2H), 7.9-7.6 (m, 2H), 7.6-7.3 (m, 2H), 7.0-6.6 (m, 2H), 5.35 (s) and 5.05(s) (1H), 4.40 (s) and 4.24 (s) (2H), 3.98 (s, 2H), 3.6-3.3 (m, 2H), 3.21 (s) and 3.02 (s) (2H), 1.28 (s) and 1.18 (s) (9H).

The route from 1d to 4d was as follows.

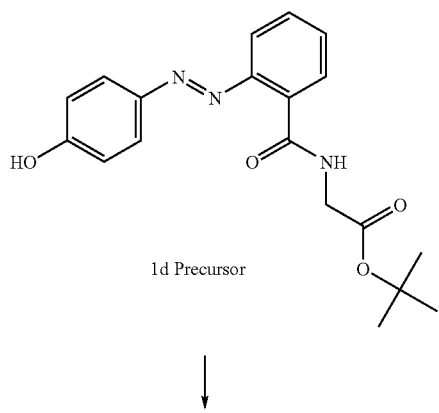

1d Precursor

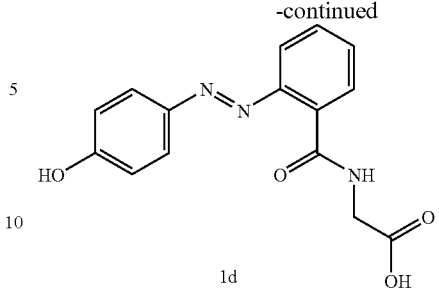

1d

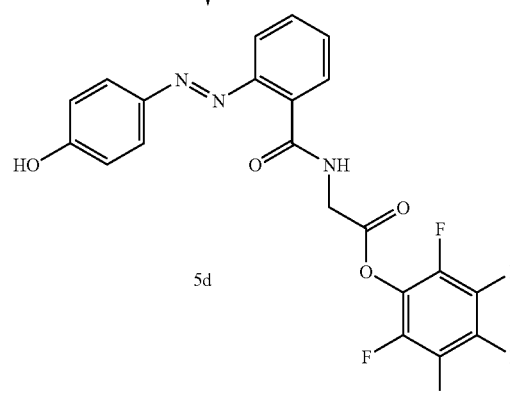

5d

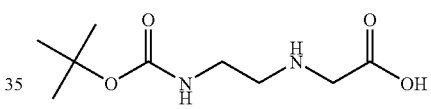

6

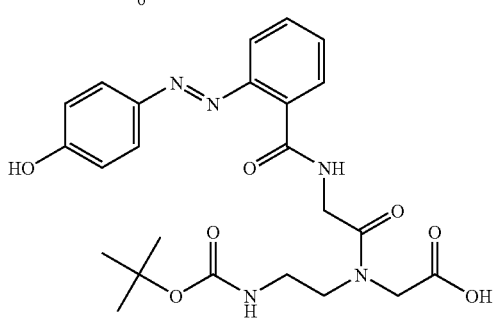

4d

Example 9

Synthesis of FAM-Gly-$^{Boc}$PNA-OH 5,6-FAM N-hydroxysuccinimide ester (50 mg, 0.11 mmol) and triethylamine (250 μL, 2.0 mmol) were added in that order to a dimethylformamide solution (5 mL) of Gly-$^{Boc}$PNA-OH (30.3 mg, 0.10 mmol) and stirred at room temperature for 15 hours. After completion of the reaction, the mixture was concentrated under reduced pressure, and the residue was subjected to silica gel column chromatography (0-25% MeOH/dichloromethane) to give FAM-Gly-$^{Boc}$PNA-OH (69.8 mg, 100%) as a yellow powder. FABMS m/z 634 [(M+H)$^+$]; HRMS (FAB$^+$) calcd. for C$_{32}$H$_{32}$O$_{11}$N$_3$ [(M+H)$^+$] 634.1959, observed 634.2034.

Example 10

Synthesis of TAMRA-Gly-$^{Boc}$PNA-OH 5,6-TAMRA N-hydroxysuccinimide ester (5 mg, 9.5 µmol) and triethylamine (20 µL, 140 µmol) were added in that order to a dimethylformamide solution (5 mL) of Gly-$^{Boc}$PNA-OH (5.8 mg, 21 µmol) and stirred at room temperature for 15 hours. After completion of the reaction, the mixture was concentrated under reduced pressure, and the residue was subjected to silica gel column chromatography (0-30% MeOH/dichloromethane) to give TAMRA-Gly-$^{Boc}$PNA-OH (6 mg, 100%) as reddish purple powder. FABMS mlz 688 [(M+H)$^+$]; HRMS (FAB$^+$) calcd. for C$_{36}$H$_{42}$O$_9$N$_5$ [(M+H)$^+$] 688.2904, observed 688.2993.

Example 11

Synthesis of ROX-Gly-$^{Boc}$PNA-OH 5,6-ROX N-hydroxysuccinimide ester (5 mg, 8 µmol) and triethylamine (20 µL, 140 µmol) were added in that order to a dimethylformamide solution (5 mL) of Gly-$^{Boc}$PNA-OH (4.9 mg, 18 µmol) and stirred at room temperature for 15 hours. After completion of the reaction, the mixture was concentrated under reduced pressure, and the residue was subjected to silica gel column chromatography (0-30% MeOH/dichloromethane) to give ROX-Gly-$^{Boc}$PNA-OH (6 mg, 100%) as a purple powder. FABMS m/z 792 [(M+H)$^+$]; HRMS (FAB$^+$) calcd. for C$_{44}$H$_{50}$O$_9$N$_5$ [(M+H)$^+$] 792.3530, observed 792.3615.

Example 12

Synthesis of 2,3,4,5,6-pentafluorophenyl N-(4-dimethylaminoazobenzene-2'-carbonyl) glycinate (o-MR-Gly-Opfp)

DCC (308 mg, 1.5 mmol) was added to a DMF solution (10 mL) of o-MR-Gly-OH (326 mg, 1 mmol) and PfpOH (276 mg, 1.5 mmol) while ice cooling, and the reaction mixture was stirred at room temperature for 15 hours. The reaction mixture was filtered, the filtrate was concentrated under reduced pressure and the residue was purified by silica gel column chromatography (0-5% acetone/CH$_2$Cl$_2$) to give o-MR-Gly-OPfp (449 mg, 91%) as an orange powder. $^1$H NMR (CDCl$_3$) δ 10.14 (brt, 1H), 8.37 (d, J=8 Hz, 1H), 7.78 (d, J=9 Hz, 2H), 7.76 (d, J=8 Hz, 1H), 7.57 (t, J=8 Hz, 1H), 7.50 (t, J=8 Hz, 1H), 6.74 (d, J=9 Hz, 2H), 4.68 (d, J=5 Hz, 2H), 3.06 (s, 6H).

Example 13

Synthesis of 2-(N-(2-((tert-butoxy)carbonylamino)ethyl)-2-(4-dimethylaminoazobenzene-2'-carbonylamino)acetylamino)acetic acid (o-MR-Gly-$^{Boc}$PNA-OH)

Diisopropylethylamine (85 µL, 0.5 mmol) was added to a DMF solution (5 mL) of o-MR-Gly-OPfp (246 mg, 0.5 mmol) and $^{Boc}$PNA-OH (109 mg, 0.5 mmol) and stirred at room temperature for 15 hours. This was concentrated under reduced pressure, and the residue was purified by silica gel column chromatography (0-30% MeOH/CH$_2$Cl$_2$) to give o-MR-Gly-$^{Boc}$PNA-OH (225 mg, 72%). $^1$H NMR (CDCl$_3$) δ 9.99 (s) and 9.85 (s) (1H), 8.3-7.6 (m) (4H), 7.4-7.2 (m) (2H), 6.67 (s) and 6.59 (s) (2H), 5.62 (s) and 5.27 (s) (1H), 4.35 (s) and 4.20 (s) (2H), 3.99 and 3.90 (2H), 3.5 (brs) and 3.3 (brs) (2H), 3.2 (brs) and 3.0 (brs) (2H), 2.99 (s) and 2.87 (s) (6H), 1.25 (brs, 9H).

Example 14

Synthesis of 2-(N-(2-((tert-butoxy)carbonylamino)ethyl)-2(4-dimethylaminoazobenzene-4'-carbonylamino)acetylamino)acetic acid (Dabcyl-Gly-$^{Boc}$PNA-OH (p-MR-Gly-$^{Boc}$PNA-OH))

Dabcyl N-hydroxysuccinimide ester (145 mg, 0.40 mmol) and triethylamine (600 µL, 4.5 mmol) were added in that order to a dimethylformamide solution (10 mL) of Gly-$^{Boc}$PNA-OH (100 mg, 0.39 mmol) and stirred at room temperature for 15 hours. After completion of the reaction, the mixture was concentrated under reduced pressure, and the residue was purified by silica gel column chromatography (0-4% MeOH/dichloromethane) to give Dabcyl-Gly-$^{Boc}$PNA-OH (184 mg, 90%) as a reddish brown powder. $^1$H NMR (DMSO-d$_6$) δ 8.18 (d, J=7 Hz, 2H), 7.91 (d, J=7 Hz, 2H), 7.88 (d, J=7 Hz, 2H), 6.77 (d, J=7 Hz, 2H), 5.76 (s) and 5.30 (s) (2H), 4.22 (brs) and 4.05 (brs) (2H), 3.73 (brs) and 3.49 (brs) (2H), 3.47 (brs) and 3.29 (brs) (2H), 1.26 (s, 9H); FABMS m/z 527 [(M+H)$^+$].

Example 15

Synthesis of N-(4-hydroxyazobenzene-2'-carbonyl) glycine (HABA-Gly-OH)

Triethylamine (732 µL, 5.25 mmol) was added to a DMF solution (10 mL) of HABA (1.21 g, 5 mmol) and t-butylglycine hydrochloride (880 mg, 5.25 mmol), while ice cooling DCC (1.13 g, 5.5 mmol) was then added thereto and the mixture was stirred for 30 minutes and further at room temperature for 15 hours. The reaction mixture was filtered, the filtrate was concentrated under reduced pressure, and the residue was purified by silica gel column chromatography (0-5% Acetone/CH$_2$Cl$_2$) to give the t-butyl ester derivative of HABA-Gly-OH (1.73 g, 97%) as an orange powder. This (1.07 g, 3 mmol) was added to formic acid (50 mL) and stirred at room temperature for 2 days, concentrated under reduced pressure to remove the formic acid, and the residue was purified by silica gel column chromatography (0-5% acetone/CH$_2$Cl$_2$) to give HABA-Gly-OH (0.89 g, 99%) as an orange powder. $^1$H NMR (CDCl$_3$) δ 10.45 (brt, 1H), 8.88 (brt, J=5 Hz, 1H), 7.91 (d, J=9 Hz, 2H), 7.85 (d, J=8 Hz, 1H), 7.70 (d, J=8 Hz, 1H), 7.60 (t, J=8 Hz, 1H), 7.57 (t, J=8 Hz, 1H), 6.94 (d, J=9 Hz, 2H), 4.05 (d, J=5 Hz, 2H); $^{13}$C NMR (CDCl$_3$) δ 171.18, 166.44, 161.54, 149.13, 145.34, 133.20, 131.09, 130.18, 129.61, 125.86, 116.00, 115.88, 41.60.

Example 16

Synthesis of 2,3,4,5,6-pentafluorophenyl N-(4-hydroxyazobenzene-2'-carbonyl)glycinate (HABA-Gly-Opfp)

DCC (308 mg, 1.5 mmol) was added to a DMF solution (10 mL) of HABA-Gly-OH (299 mg, 1 mmol) and PfpOH (276 mg, 1.5 mmol) while ice cooling, and the reaction mixture was stirred at room temperature for 15 hours. The reaction mixture was filtered, the filtrate was concentrated under reduced pressure, and the residue was purified by silica gel column chromatography (0-5% acetone/CH$_2$Cl$_2$) to give HABA-Gly-OPfp (46 mg, 10%) as an orange powder. $^1$H NMR (CDCl$_3$) δ 9.67 (brs, 1H), 9.02 (brt, 1H), 7.8-7.7 (m, 3H), 7.6-7.5 (m, 2H), 7.23 (d, J=9 Hz, 1H), 6.86 (d, J=9 Hz, 2H), 4.67 (d, J=5 Hz, 2H).

Example 17

Synthesis of 2-(N-(2-((tert-butoxy)carbonylamino) ethyl)-2-(4-hydroxyazobenzene-2'-carbonylamino) acetylamino)acetic acid (HABA-Gly-$^{Boc}$PNA-OH)

Diisopropylethylamine (14 mL, 80 μmol) was added to a DMF solution (5 mL) of HABA-Gly-OPfp (37 mg, 80 μmol) and $^{Boc}$PNA-OH (18 mg, 80 μmol) and stirred at room temperature for 15 hours. This was concentrated under reduced pressure, and the residue was purified by silica gel column chromatography (0-30% MeOH/CH$_2$Cl$_2$) to give HABA-Gly-$^{Boc}$PNA-OH (13 mg, 33%). $^1$H NMR (CDCl$_3$) δ 9.77 (s) and 9.59 (s) (1H), 8.26 (s) and 8.14 (s) (2H); 7.9-7.6 (m, 2H), 7.6-7.3 (m, 2H), 7.0-6.6 (m, 2H), 5.35 (s) and 5.05 (s) (1H), 4.40 (s) and 4.24 (s) (2H), 3.98 (s, 2H) 3.6-3.3 (m, 2H), 3.21 (s) and 3.02 (s) (2H), 1.28 (s) and 1.18 (s) (9H).

Example 18

Synthesis of 2,3,4,5,6-pentafluorophenyl 2-(5,7,8-trimethyl-1,3-dioxo-2,5-dihydro-2,4-diazaphenazin-2-yl)acetate (Flavin-Opfp)

EDC (73.2 mg, 382 μmol) was added to a DMF solution (10 mL) of Flavin (100 mg, 318 μmol) and PfpOH (70.2 mg, 381 μmol) at 0° C., and the reaction mixture was stirred at 0° C. for 1 hour and at room temperature for 12 hours. The reaction mixture was concentrated under reduced pressure, and the residue was subjected to partition extraction with a water-chloroform system. The organic layer was dried with magnesium sulphate and concentrated under reduced pressure, and the residue was purified by silica gel column chromatography (2.5% MeOH/CHCl$_3$) to give Flavin-OPfp (130 mg, 85%). $^1$H NMR (CDCl$_3$) δ 8.07 (s, 1H), 7.44 (s, 1H), 5.21 (s, 2H), 4.14 (s, 3H), 2.55 (s, 3H), 2.45 (s, 3H); HRMS (FAB$^+$, NBA/CH$_2$Cl$_2$) calcd. for C$_{21}$H$_{14}$O$_4$N$_4$F$_5$ [(M+H)$^+$] 481.0934, observed 481.0950; UV λmax (DMF) 390, 460 (nm)

Example 19

Synthesis of 2-(N-(2-((tert-butoxy)carbonylamino) ethyl)-2-(5,7,8-trimethyl-1,3-dioxo(2,5-dihydro-2,4-di-azaphenazin-2-yl)acetylamino)acetic acid (Flavin-$^{Boc}$PNA-OH)

Diisopropylethylamine (36.3 μL, 208 μmol) was added to a DMF solution (10 mL) of Flavin-OPfp (100 mg, 208 μmol) and $^{Boc}$PNA-OH (45.4 mg, 208 μmol) and stirred at room temperature for 15 hours. This was concentrated under reduced pressure, and the residue was purified by silica gel column chromatography (10-50% MeOH/CHCl$_3$) to give Flavin-$^{Boc}$PNA-OH (130 mg, 85%). $^1$H NMR (CD$_3$OD) δ 7.94 (s) and 7.86 (s) (1H), 7.80 (s) and 7.75 (s) (1H), 5.03 (s) and 4.88 (s) (2H), 4.17 (s) and 4.13 (s) (3H), 3.64 and 3.52 (2H), 3.38 and 3.26 (2H), 2.58 (s) and 2.56 (s) (3H), 2.46 (s) and 2.44 (s) (3H), 1.46 (s) and 1.41 (s) (9H); HRMS (FAB$^+$, NBA/CH$_2$Cl$_2$) calcd. for C$_{24}$H$_{31}$O$_7$N$_6$ [(M+H)$^+$] 515.2252, observed 515.2273; UV λmax (DMF) 390, 460 (nm).

Example 20

Synthesis of 2',3',4',5',6'-pentafluorophenyl 1,3-di-oxo-1H-benz[de]isoquinoline-2 (3H)-acetate (NI-Opfp)

DCC (155 mg, 0.75 mmol) was added to a DMF solution (5 mL) of NI—OH (192 mg, 0.75 mmol) and PfpOH (152 mg, 0.83 mmol) while ice cooling, and the reaction mixture was stirred at room temperature for 15 hours. The reaction mixture was filtered, the filtrate was concentrated under reduced pressure, and the residue was purified by silica gel column chromatography (CH$_2$Cl$_2$) to give NI-OPfp (277 mg, 87%) as a red powder. $^1$H NMR (CDCl$_3$) δ 8.64 (d, J=8 Hz, 2H), 8.25 (d, J=8 Hz, 2H), 7.78 (t, J=8 Hz, 2H), 5.29 (s, 2H).

Example 21

Synthesis of 2-(N-(2-((tert-butoxy)carbonylamino) ethyl)-2-(1,3-dioxo-1H-benz[de]isoquinoline-2(3H)) acetylamino)acetic acid (NI-$^{Boc}$PNA-OH)

Diisopropylethylamine (87 μL, 0.50 mmol) was added to a DMF solution (10 mL) of NI-OPfp (211 mg, 0.50 mmol) and $^{Boc}$PNA-OH (120 mg, 0.55 mmol) and stirred at room temperature for 15 hours. This was concentrated under reduced pressure, and the residue was purified by silica gel column chromatography (0-20% MeOH/CHCl$_3$) to give NI-$^{Boc}$PNA-OH (130 mg, 85%). $^1$H NMR (DMSO-d$_6$) δ 8.47 (m, 4H), 7.86 (dd, J=8.3, 7.3 Hz, 2H), 4.73 (s, 2H); $^{13}$C NMR (CDCl$_3$) δ 167.84, 163.59, 134.20, 131.44, 131.39, 128.11, 126.78, 122.00, 61.59, 41.44, 14.29; HRMS (FAB$^+$, NBA/CH$_2$Cl$_2$) calculated for (C$_{16}$H$_{13}$NO$_4$)H$^+$ 284.2933, observed 456.1767; UV λmax (DMF) 333 nm.

Example 22

Synthesis of 2',3',4',5',6'-pentafluorophenyl 1,3-di-oxo-5-nitro-1H-benz[de]isoquinoline-2(3H)-acetate (NI(NO$_2$)-Opfp)

EDC (73.2 mg, 382 μmol) was added to a DMF solution (10 mL) of NI(NO$_2$)—OH (100 mg, 318 μmol) and PfpOH (70.2 mg, 381 μmol) at 0° C., and the reaction mixture was stirred at 0° C. for 1 hour and at room temperature for 12 hours. The reaction mixture was concentrated under reduced pressure, and the residue was subjected to partition extraction with a water-chloroform system. The organic layer was dried with magnesium sulphate and concentrated under reduced pressure, and the residue was purified by silica gel column chromatography (2.5% MeOH/CHCl$_3$) to give NI(NO$_2$)-OPfp (130 mg, 85%). $^1$H NMR (CDCl$_3$) δ 8.07 (s, 1H), 7.44 (s, 1H), 5.21 (s, 2H), 4.14 (s, 3H), 2.55 (s, 3H), 2.45 (s, 3H); HRMS (FAB$^+$, NBA/CH$_2$Cl$_2$) calcd. for C$_{21}$H$_{14}$O$_4$N$_4$F$_5$ [(M+H)$^+$] 481.0934, observed 481.0950; UV λmax (DMF) 390, 460 (nm).

Example 23

Synthesis of 2-(N-(2-((tert-butoxy)carbonylamino)ethyl)-2-(1,3-dioxo-5-nitro-1H-benz[de]isoquinoline-2(3H))acetylamino)acetic acid (NI(NO$_2$)-$^{Boc}$PNA-OH)

Diisopropylethylamine (36.3 µL, 208 µmol) was added to a DMF solution (10 mL) of NI(NO$_2$)-OPfp (100 mg, 208 µmol) and $^{Boc}$PNA-OH (45.4 mg, 208 µmol) and stirred at room temperature for 15 hours. This was concentrated under reduced pressure and the residue was purified by silica gel column chromatography (10-50% MeOH/CHCl$_3$) to give NI(NO$_2$)-$^{Boc}$PNA-OH (130 mg, 85%). $^1$H NMR (CD$_3$OD) δ 7.94 (s) and 7.86 (s) (1H), 7.80 (s) and 7.75 (s) (1H), 5.03 (s) and 4.88 (s) (2H), 4.17 (s) and 4.13 (s) (3H), 3.64 and 3.52 (2H), 3.38. and 3.26 (2H), 2.58 (s) and 2.56 (s) (3H), 2.46 (s) and 2.44 (s) (3H), 1.46 (s) and 1.41 (s) (9H); HRMS (FAB$^+$, NBA/CH$_2$Cl$_2$) calcd. for C$_{24}$H$_{31}$O$_7$N$_6$ [(M+H)$^+$] 515.2252, observed 515.2273; UV λmax (DMF) 390, 460 (nm).

Example 24

Synthesis of 5-acetylamino-1,3-dioxo-1H-benz[de]isoquinoline-2(3H)-acetic Acid (NI(NHAc)—OH)

NI(NH$_2$)—OH (100 mg, 0.37 mmol) was dissolved in pyridine (3 mL) and Ac$_2$O (3 mL) and stirred at room temperature for 15 hours. The mixture was concentrated under reduced pressure, then washed with dichloromethane, filtered and dried to give NI(NHAc)—OH (103.2 mg, 89%). $^1$H NMR (DMSO-d$_6$) δ 8.79 (s, 1H), 8.61 (s, 1H), 8.40 (d, J=8 Hz, 1H), 8.37 (d, J=8 Hz, 1H), 7.82 (t, J=8 Hz, 1H), 4.71 (s, 2H), 2.16 (s, 3H).

Example 25

Synthesis of 2',3',4',5',6'-pentafluorophenyl 5-acetylamino-1,3-dioxo-1H-benz[de]isoquinoline-2(3H)-acetate (NI(NHAc)-Opfp)

DCC (71 mg, 0.34 mmol) was added to a DMF solution (5 mL) of NI(NHAc)—OH (97 mg, 0.31 mmol) and PfpOH (63 mg, 0.34 mmol) at 0° C. and the reaction mixture was stirred at 0° C. for 1 hour and at room temperature for 15 hours. The reaction mixture was filtered and then concentrated under reduced pressure, and the residue was purified by silica gel column chromatography (0-20% acetone/CHCl$_3$) to give NI(NHAc)-OPfp (140 mg, 95%). $^1$H NMR (CDCl$_3$) δ 8.96 (s, 1H), 8.53 (d, J=7.7 Hz, 1H), 8.32 (d, J=1.6 Hz, 1H), 8.20 (d, J=7.7 Hz, 1H), (t, J=7.5 Hz, 2H), 7.82 (brs, 1 H), 7.74 (d, J=7.7 Hz, 1H), 5.27 (s, 2H), 2.28 (s, 3H).

Example 26

Synthesis of 2-(N-(2-((tert-butoxy)carbonylamino)ethyl)-2-(5-acetylamino-1,3-dioxo-1H-benz[de]isoquinoline-2(3H))acetylamino)acetic acid (NI(NHAc)-$^{Boc}$PNA-OH)

Diisopropylethylamine (54 µL, 0.30 mmol) was added to a DMF solution (5 mL) of NI(NHAc)-OPfp (140 mg, 0.29 mmol) and $^{Boc}$PNA—OH (67 mg, 0.30 mmol) and stirred at room temperature for 15 hours. This was concentrated under reduced pressure, and the residue was purified by silica gel column chromatography (2-20% MeOH/CHCl$_3$) to give NI(NHAc)-$^{Boc}$PNA-OH (117 mg, 85%). $^1$H NMR (DMSO-d$_6$) δ 8.4-7.3 (m, 5H), 5.05 (brs) and 4.90 (brs) (2H), 3.76 (brs) and 3.54 (brs) (2H), 3.64 (s) and 3.49 (s) (2H), 3.54 (brs) and 3.41 (brs) (2H), 2.15 (s) and 2.04 (s) (3H), 1.48 (s) and 1.45 (s) (9H).

Example 27

Synthesis of succinimidyl N-4-dimethylaminoazobenzene-3'-carbonate (m-MR-Osu)

DCC (100 mg, 0.50 mmol) was added to a DMF solution (7 mL) of m-methyl Red (m-MR-OH; 110 mg, 0.41 mmol) and N-hydroxysuccinimide (60 mg, 0.52 mmol) at 0° C., and the reaction mixture was stirred for 30 minutes and then at room temperature for 15 hours. The reaction mixture was filtered and distilled under reduced pressure, and the residue was subjected to silica gel column chromatography (CH$_2$Cl$_2$) to give m-MR—OSu (124 mg; 82%) as an orange powder. $^1$H NMR (CDCl$_3$) δ 8.59 (s, 1H), 8.13 (t, J=9.1 Hz, 2H), 7.90 (d, J=9.1 Hz, 2H), 7.61 (t, J=7.9 Hz, 1H), 6.77 (d, J=9.1 Hz, 2H), 3.11 (s, 6H), 2.93 (brs, 4H)

Example 28

Synthesis of 2-(N-(2-((tert-butoxy)carbonylamino)ethyl)-2-(4-dimethylaminoazobenzene-3'-carbonylamino)acetylamino)acetic acid (m-MR-Gly-$^{Boc}$PNA-OH)

m-MR-OSu (73 mg, 0.20 mmol) and triethylamine (350 µL, 2.7 mmol) were added in that order to a DMF solution (10 mL) of Gly-$^{Boc}$PNA-OH (50 mg, 0.18 mmol) and stirred at room temperature for 15 hours. After completion of the reaction, the mixture was concentrated under reduced pressure, and the residue was subjected to silica gel column chromatography (0-10% MeOH/dichloromethane) to give m-MR-Gly-$^{Boc}$PNA-OH (95 mg, 100%) as an orange powder. $^1$H NMR (DMSO-d$_6$) δ 8.26 (s, 1H), 7.92 (d, J=7.6 Hz, 2H) 7.83 (d, J=9.1 Hz, 2H), 7.62 (t, J=7.6 Hz, 1H), 6.88 (brt) and 6.74 (brt) (1H), 6.85 (d, J=9.1 Hz, 2H), 4.22 (d, J=2.7 Hz, 2H); 3.99 (s) and 3.89 (s) (2H), 3.44 (t, J=6.4 Hz, 1H), 3.4-3.25 (brs, 4H), 3.07 (s, 6H), 1.39 (s) and 1.37 (s) (9H).

Example 29

Synthesis of 2-(N-(2-((tert-butoxy)carbonylamino)ethyl)-N'-((1-pyrenyl-n-butyl)glycyl))acetic acid (Pyrene-Gly-$^{Boc}$PNA-OH).

Pyrene-OSu (39 mg, 0.10 mmol) and triethylamine (138 µL, 1.0 mmol) were added in that order to a DMF solution (5 mL) of Gly-$^{Boc}$PNA-OH (25 mg, 0.09 mmol) and stirred at room temperature for 15 hours. After completion of the reaction, the mixture was concentrated under reduced pressure, and the residue was subjected to silica gel column chromatography (0-10% MeOH/dichloromethane) to give Pyrene-Gly-$^{Boc}$PNA-OH (30 mg, 61%) as a pale yellow powder. HRMS (FAB$^+$) calcd. for C$_{31}$H$_{35}$O$_6$N$_3$Na [(M+Na)$^+$] 568.2526, observed 568.2429.

Example 30

Synthesis of 2-(N-(2-((tert-butoxy)carbonylamino)ethyl)-2-(7-diethylaminocoumarin-3-carbonyl)glycyl)acetic acid (Coumarin-Gly-$^{Boc}$PNA-OH)

Coumarin-OSu (15 mg, 0.042 mmol) and triethylamine (55.5 μL, 0.4 mmol) were added in that order to a DMF solution (5 mL) of Gly-$^{Boc}$PNA-OH (12.7 mg, 0.046 mmol) and stirred at room temperature for 15 hours. After completion of the reaction, the mixture was concentrated under reduced pressure, and the residue was subjected to silica gel column chromatography (0-20% MeOH/dichloromethane) to give Coumarin-Gly-$^{Boc}$PNA-OH (23 mg, 100%) as a yellow powder. $^1$H NMR (DMSO-d$_6$) δ 8.68 (s) and 8.66 (s) (1H), 7.70 and 7.69 (each d, J=9.1 Hz) (1H), 6.89 (brt) and 6.75 (brt) (1H), 6.80 (d, J=9.1 Hz, 1H), 6.62 (s, 1H), 4.25 (brd) and 4.07 (brd) (2H), 4.13 (m, 1H), 3.98 (s) and 3.89 (s) (2H), 3.48 (q, J=6.8 Hz, 4H), 3.35 (m, 2H), 3.13 (brq) and 3.07 (brq) (2H), 1.37 (s) and 1.36 (s) (9H), 1.14 (t, J=6.8 Hz, 6H).

INDUSTRIAL APPLICABILITY

The novel functional PNA monomers in accordance with the present invention can be applied to the assembly of PNA that is used in, for example, gene therapy. Furthermore, in accordance with the present invention, a functional molecule can be efficiently introduced into PNA by two complementary synthetic routes B and C to the functional PNA monomers. The present invention can therefore be applied industrially, for example to an industrial synthesis of a functional PNA monomer unit using a Boc type monomer unit or a benzyloxycarbonyl-ω-amino acid derivative.

The invention claimed is:

1. A compound represented by general formula (I) below:

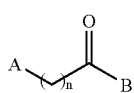

(in the formula, A denotes

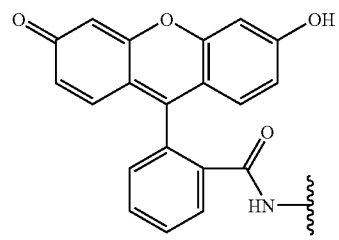

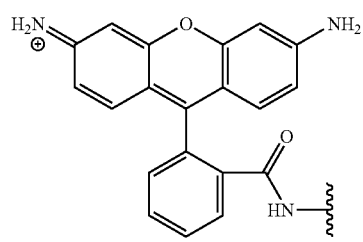

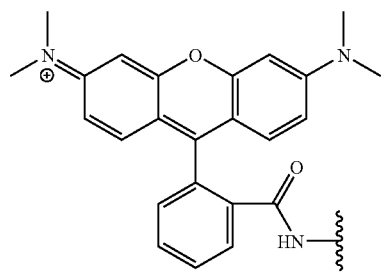

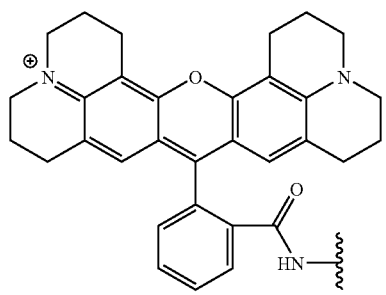

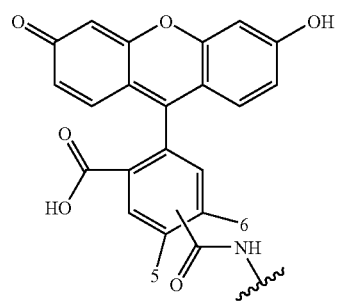

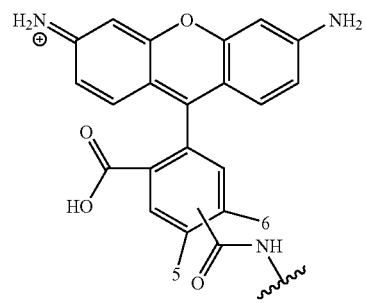

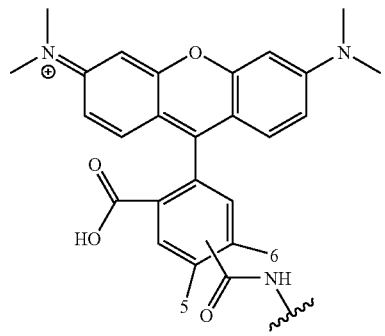

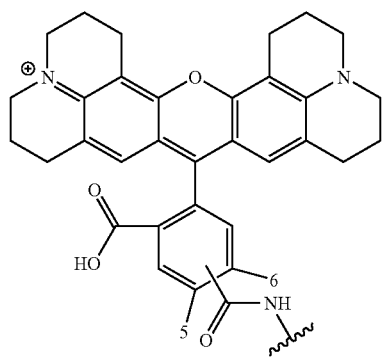
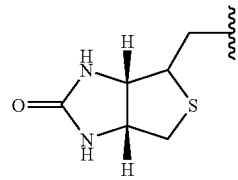
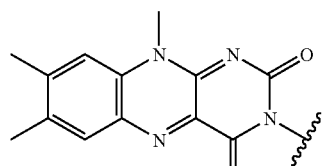
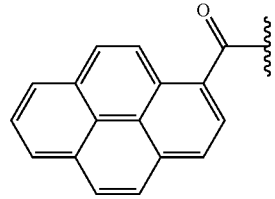
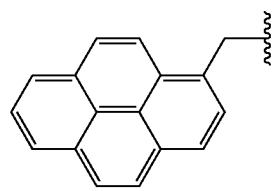
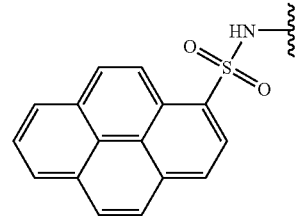
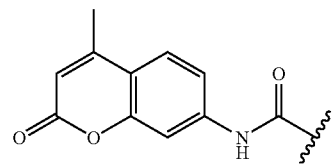
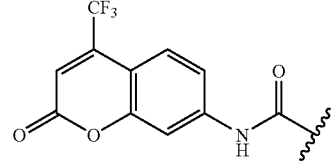
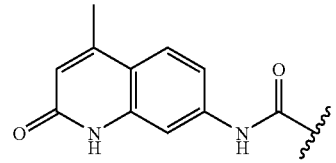
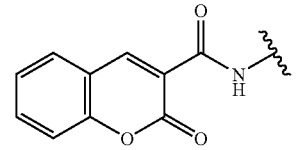

-continued
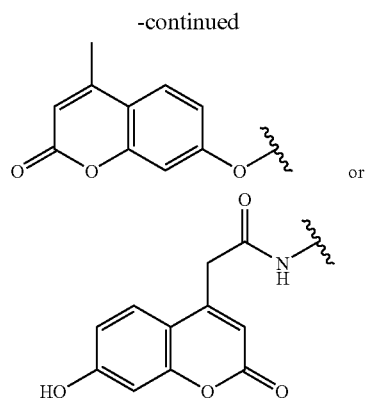
or
B denotes
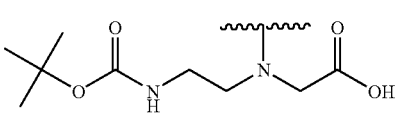
n is an integer of 1 to 4, wherein A denotes
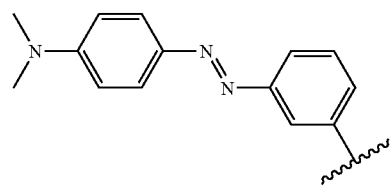
then B denotes
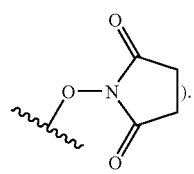
.
* * * * *